US008377864B2

(12) United States Patent
Catelas et al.

(10) Patent No.: US 8,377,864 B2
(45) Date of Patent: Feb. 19, 2013

(54) FIBRIN GEL FOR CONTROLLED RELEASE OF PDGF AND USES THEREOF

(75) Inventors: Isabelle Catelas, Ottawa (CA); Joseph Dwyer, Grayslake, IL (US); Wanda Seyton, Lake Zurich, IL (US); Shane Donovan, Lake Geneva, WI (US); Sam L. Helgerson, Lincolnshire, IL (US)

(73) Assignees: Baxter International Inc., Deerfield, IL (US); Baxter Healthcare SA, Wallisellen (CH)

( * ) Notice: Subject to any disclaimer, the term of this patent is extended or adjusted under 35 U.S.C. 154(b) by 901 days.

(21) Appl. No.: 12/142,734

(22) Filed: Jun. 19, 2008

(65) Prior Publication Data

US 2009/0075881 A1 Mar. 19, 2009

Related U.S. Application Data

(60) Provisional application No. 60/936,198, filed on Jun. 19, 2007.

(51) Int. Cl.
*A61K 38/00* (2006.01)
*A61K 38/18* (2006.01)
*A61K 38/43* (2006.01)
*A61K 38/48* (2006.01)
*A61P 17/02* (2006.01)
*A61K 35/14* (2006.01)
*C07K 1/00* (2006.01)
*C07K 17/00* (2006.01)

(52) U.S. Cl. .......... 514/1.1; 514/8.2; 514/9.4; 424/94.1; 424/94.64; 530/350; 530/381; 530/382

(58) Field of Classification Search .................. 514/1.1, 514/8.2, 9.4; 424/94.1, 94.64; 530/350, 530/381, 382
See application file for complete search history.

(56) References Cited

U.S. PATENT DOCUMENTS

| 4,391,904 | A | 7/1983 | Litman et al. |
| 5,716,645 | A | 2/1998 | Tse et al. |
| 5,962,405 | A | 10/1999 | Seelich |
| 6,506,365 | B1 | 1/2003 | Redl et al. |
| 6,511,958 | B1 * | 1/2003 | Atkinson et al. ............ 424/94.4 |
| 6,579,537 | B2 | 6/2003 | Seelich et al. |
| 6,696,073 | B2 | 2/2004 | Boyce et al. |
| 6,713,453 | B2 | 3/2004 | Redl et al. |
| 6,965,014 | B1 | 11/2005 | Delmotte et al. |
| RE39,298 | E | 9/2006 | MacPhee et al. |
| 7,122,057 | B2 | 10/2006 | Beam et al. |
| 7,241,603 | B2 | 7/2007 | Seelich et al. |
| 2003/0012818 | A1 | 1/2003 | Schense et al. |

FOREIGN PATENT DOCUMENTS

| JP | 3604688 | 12/2004 |
| KR | 20070095288 A | 9/2007 |
| WO | WO-92/09301 A1 | 6/1992 |
| WO | WO-99/11301 | 3/1999 |
| WO | WO-03/041568 A2 | 5/2003 |
| WO | WO-2006/042311 A2 | 4/2006 |
| WO | WO-2006044334 A2 | 4/2006 |

OTHER PUBLICATIONS

Arnaud et al. Potentiation of transforming growth factor (TGF-beta 1) by natural coral and fibrin in a rabbit cranioplasty model. *Calcif. Tissue Int.* 54: 493-8 (1994).
Arnaud et al., Osteogenesis induced by the combination of growth factor, fibrin glue and coral; towards a substitute of autologous bone graft. An experimental study on the rabbit. *Ann. Chir. Plast. Esthet.* 39: 491-8 (1994).
Baron et al., The oligodendrocyte precursor mitogen PDGF stimulates proliferation by activation of alpha(v)beta3 integrins. *EMBO. J.* 21: 1957-66 (2002).
Betsholtz et al., Developmental roles of platelet-derived growth factors. *Bioessays.* 23: 494-507 (2001).
Blomback et al., Purification of human and bovine fibrinogen. *Arkiv. Kemi.* 10: 415-443 (1959).
Caldwell et al., Growth factors regulate the survival and fate of cells derived from human neurospheres. *Nat. Biotechnol.* 19: 475-9 (2001).
Cao et al., Angiogenesis stimulated by PDGF-CC, a novel member in the PDGF family, involves activation of PDGFR-alphaalpha and -alphabeta receptors. *FASEB. J.* 16: 1575-83 (2002).
Caplan, Mesenchymal stem cells. *J. Orthop Res.* 9: 641-50 (1991).
Catelas et al., Human mesenchymal stem cell proliferation and osteogenic differentiation in fibrin gels in vitro. *Tissue Eng.* 12: 2385-96 (2006).
Cox et al., Behavior of human dermal fibroblasts in three-dimensional fibrin clots: dependence on fibrinogen and thrombin concentration. *Tissue Eng.* 10: 942-54 (2004).
De Marchis et al., Platelet-derived growth factor inhibits basic fibroblast growth factor angiogenic properties in vitro and in vivo through its alpha receptor. *Blood* 99: 2045-53 (2002).
Fiedler et al., To go or not to go: Migration of human mesenchymal progenitor cells stimulated by isoforms of PDGF. *J. Cell. Biochem.* 93: 990-98 (2004).
Fortier et al., Altered biological activity of equine chondrocytes cultured in a three-dimensional fibrin matrix and supplemented with transforming growth factor beta-1. *Am. J. Vet. Res.* 58: 66-70 (1997).
Gelberman et al., The early effects of sustained platelet-derived growth factor administration on the functional and structural properties of repaired intrasynovial flexor tendons: An in vivo biomechanic study at 3 weeks in canines. *J. Hand. Surg.* 32A: 373- (2007).
Giannoni et al., Release kinetics of transforming growth factor-beta1 from fibrin clots. *Biotechnol. Bioeng..* 83: 121-3 (2003).

(Continued)

Primary Examiner — Ganapathirama Raghu
(74) Attorney, Agent, or Firm — Marshall, Gerstein & Borun LLP

(57) ABSTRACT

The present invention relates, in general, to fibrin sealants, which contain platelet derived growth factor (PDGF) for controlled release in situ for therapeutic applications, including musculoskeletal disorders, soft tissue disorders and vascular diseases.

35 Claims, 14 Drawing Sheets

OTHER PUBLICATIONS

Guehennec et al., A review of bioceramics and fibrin sealant. *Eur. Cells Mater.* 8: 1-11 (2004).

Heldin et al., Mechanism of action and in vivo role of platelet-derived growth factor. *Physiol. Rev.* 79: 1283-316 (1999).

Isner et al., Myocardial gene therapy. *Nature.* 415: 234-9 (2002).

Leitner et al., Platelet content and growth factor release in platelet-rich plasma: A comparison of four different systems. *Vox. Sang.* 91: 135-9 (2006).

Mehrotra et al., Differential regulation of platelet-derived growth factor stimulated migration and proliferation in osteoblastic cells. *J. Cell. Biochem.* 93: 741-52 (2004).

Palumbo et al., Different effects of high and low shear stress on platelet-derived growth factor isoform release by endothelial cells: consequences for smooth muscle cell migration. *Arterioscler. Thromb. Vasc. Biol.* 22: 405-11 (2002).

Pitas et al., Anti-phencyclidine monoclonal antibody binding capacity is not the only determinant of effectiveness, disproving the concept that antibody capacity is easily surmounted. *Drug Metab. Dispos.* 34: 906-12 (2006).

Shreiber et al., Effects of PDGF-BB on rat dermal fibroblast behavior in mechanically stressed and unstressed collagen and fibin gels. *Exp. Cell. Res.* 266: 155-66 (2001).

Sierra, Fibrin sealant adhesive systems: a review of their chemistry, material properties and clinical applications. *J. Biomater Appl.* 7: 309-30 (1993).—Part 1.

Sierra, Fibrin sealant adhesive systems: a review of their chemistry, material properties and clinical applications. *J. Biomater Appl.* 7: 330-52 (1993).—Part 2.

Thommen et al., PDGF-BB increases endothelial migration on cord movements during angiogenesis in vitro. *J. Cell. Biochem.* 64: 403-13 (1997).

Thomopoulous et al. PDGF-BB released in tendon repair using a novel delivery system promotes cell proliferation and collagen remolding. *J. Orth. Res.* 25: 1358-68 (2007).

Vale et al., Therapeutic angiogenesis in critical limb and myocardial ischemia. *J. Interv. Cardiol.* 14: 511-28 (2001).

Willerth et al., The effects of soluble growth factors on embryonic stem cell differentiation inside of fibrin scaffolds. *Stem Cells.* 25: 2235-44 (2007).

Wong et al., Fibrin-based biomaterials to deliver human growth factors. *Thromb Haemost.* 89: 573-82 (2003).

Yazawa et al., Basic studies on the bone formation ability by platelet rich plasma in rabbits. *J. Craniofac. Surg.* 15: 439-46 (2004).

European Search Report for corresponding European Application No. 08771519.9, dated Apr. 26, 2010.

International Preliminary Report on Patentability for corresponding International Application No. PCT/US2008/067562, dated Dec. 22, 2009.

International Search Report and Written Opinion for corresponding International Application No. PCT/US2008/067562, dated Sep. 23, 2009.

\* cited by examiner

A.

B.

C.

FIBRIN GEL FOR CONTROLLED RELEASE OF PDGF AND USES THEREOF

This application claims the priority benefit of U.S. Provisional Patent application No. 60/936,198, filed Jun. 19, 2007, herein incorporated by reference in its entirety.

FIELD OF THE INVENTION

The present invention relates, in general, to fibrin sealants, which contain platelet derived growth factor (PDGF) for controlled release through reversible binding in situ for therapeutic applications, including musculoskeletal and vascular diseases.

BACKGROUND OF THE INVENTION

Fibrin sealants are a type of surgical "glue" that is made from human blood-clotting proteins, and that is typically used during surgery to control bleeding. The ingredients in these sealants interact during application to form a stable clot composed of a blood protein fibrin. Fibrin sealants are presently used during surgery for several different purposes: to control bleeding in the area where the surgeon is operating, to speed wound healing, to seal off hollow body organs or cover holes made by standard sutures, to provide slow-release delivery of medications to tissues exposed during surgery.

Fibrin sealants generally consist of two human plasma-derived components: (a) a highly concentrated Fibrinogen Complex (FC) composed primarily of fibrinogen and fibronectin along with catalytic amounts of Factor XIII and plasminogen and (b) a high potency thrombin. Fibrin sealants may also contain aprotinin. By the action of thrombin, (soluble) fibrinogen at first is converted into fibrin monomers which aggregate spontaneously and form a so-called fibrin clot. Simultaneously, factor XIII (FXIII) present in the solution is activated by thrombin in the presence of calcium ions to factor XIIIa. The aggregated fibrin monomers and any remaining fibronectin possibly present are cross-linked to form a high polymer by new peptide bonds forming. By this cross-linking reaction, the strength of the clot formed is substantially increased. Generally, the clot adheres well to wound and tissue surfaces, which leads to the adhesive and haemostatic effect. (U.S. Pat. No. 7,241,603). Therefore, fibrin adhesives are frequently used as two-component adhesives which comprise a fibrinogen complex (FC) component together with a thrombin component which additionally contains calcium ions.

A particular advantage of a fibrin sealant is that the adhesive/gel does not remain at its site of application as a foreign body, but is completely resorbed just as in natural wound healing, and is replaced by newly formed tissue. Various cells, e.g., macrophages and, subsequently, fibroblasts migrate into the gel, lyse and resorb the gel material and form new tissue. Fibrin sealants have been used to form fibrin gels in situ, and these fibrin gels have been used for delivery of cells and growth factors (Cox et al., Tissue Eng 10:942-954, 2004; Wong et al., Thromb Haemost 89:573-582, 2003).

For tissue repair, it is desirable to localize growth factors and cells in a matrix such as a fibrin gel. For example, fibrin gel has been used for delivery of TGF-β in various complex mixtures including fetal bovine serum, coral granules, and liposomes (Fortier et al., Am J Vet Res 58(1): 66-70, 1997; Arnaud et al., Chirurgie Plastique Esthetique 39(4): 491-498, 1994; Arnaud et al. Calcif Tissue Int 54: 493-498, 1994; Giannoni et al., Biotechnology and Bioengineering 83(1): 121-123, 2003). Alternative means to deliver growth factors from fibrin gels involve conjugates comprising transglutaminase substrates, antibodies, and VEGF fragments bound to the growth factors (See, for example U.S. Pat. Nos. 6,506,365; 6,713,453 and US Patent Publication 2003/0012818, incorporated herein by reference in their entirety). See also US patent application 20030012818 which describes drug delivery matrices to enhance wound healing. Additionally, fibrin gels have been shown to induce cell growth (e.g., human mesenchymal stem cell (HMSC)) and proliferation as well as, to some extent, osteogenic differentiation, depending on the concentrations of FC and thrombin in the matrix (Catelas et al., Tissue Eng 12:2385-2396, 2006).

The ability of fibrin sealants to deliver growth factors to a particular site in the body can be beneficial, but proper regrowth of tissue often requires a continuous/steady supply of growth factor or cytokine delivered at a specific rate to the site so that proper treatment is ensured. This is especially true if the therapeutic protein has a short half-life in vivo. Fibrin sealants currently in use provide for some delayed release of the seeded drug or agent, but the ability to extend the life of the agent in the sealant would improve the long-term tissue repair in vivo.

Thus, there remains a need in the art to develop an effective means to deliver growth factor in vivo for treatment of various conditions and disorders, to develop improved methods for controlled release of growth factors from a fibrin gel.

SUMMARY OF THE INVENTION

The present invention provides compositions of fibrin sealant comprising a platelet derived growth factor (PDGF) for controlled release through reversible binding of the growth factor in vitro and in vivo. The invention also provides a method to modify the release of PDGF protein from a fibrin sealant by modifying the content of fibrinogen complex (FC) component used to formulate the sealant. For the treatment of a condition or disorder, it is contemplated that the PDGF, once released from the fibrin sealant, retains its biological activity such that the PDGF can mediate its expected biological activity in vitro or in vivo.

In one aspect, the invention provides a method for modifying the release of a platelet derived growth factor (PDGF) protein, said protein selected from the group consisting of PDGF-AB and PDGF-BB from a fibrin sealant, wherein the fibrin sealant is produced by admixture of a FC component, a thrombin component and a PDGF component, the method comprising, a) determining the amount of PDGF released from a first fibrin sealant having a known initial amount of PDGF and a known final concentration of FC, and b) modifying the known final concentration of FC used in the first fibrin sealant of step (a) to produce a second fibrin sealant, wherein increasing the concentration of the FC in the second sealant compared to the known final concentration of FC in the first sealant decreases the rate of PDGF release from the second sealant as compared to the release of PDGF from the first sealant of step (a), and wherein the second sealant has the same initial amount of PDGF as the first sealant in step (a).

In a related aspect, the invention provides a method for modifying the release of a PDGF protein, said protein selected from the group consisting of PDGF-AB and PDGF-BB, from a fibrin sealant, wherein the fibrin sealant is produced by admixture of a FC component, a thrombin component and a PDGF component, the method comprising, a) determining the amount of PDGF released from a first fibrin sealant having a known initial amount of PDGF and a known final concentration of FC, and b) modifying the known final concentration of FC used in the first fibrin sealant in of step (a)

to produce a second fibrin sealant, wherein decreasing the concentration of FC in the second sealant compared to the known final concentration of FC in the first sealant increases the rate of PDGF release from the second sealant as compared to the release of PDGF from the first sealant of step (a), and wherein the second sealant has the same initial amount of PDGF as the first sealant in step (a).

In one embodiment, the final FC concentration in the first or second sealant is within the range of about 1 mg/ml to about 150 mg/ml. In a related embodiment, the final FC concentration in the first or second sealant is within the range of about 5 mg/ml to about 75 mg/ml.

In another embodiment, it is contemplated that the final FC concentration in the first fibrin sealant differs from the final FC concentration in the second sealant by about 1 mg/ml to about 149 mg/ml. In a further embodiment, the final FC concentration in the first fibrin sealant differs from the FC concentration in the second sealant by about 5 mg/ml to about 75 mg/ml. In yet another embodiment, the final FC concentration in the first fibrin sealant differs from the FC concentration in the second sealant by about 10 mg/ml to about 60 mg/ml.

It is contemplated that in some embodiments, the final concentration of the thrombin component in the first or second sealant is within the range of about 1 IU/ml to 250 IU/ml. In another embodiment, the final concentration of PDGF in the first or second sealant is in the range of about 1 ng/ml to about 1 mg/ml.

In another aspect, the invention contemplates a method for the controlled release of a PDGF protein, said protein selected from the group consisting of PDGF-AB, and PDGF-BB, in a patient in need thereof, comprising administering to said patient a fibrin sealant comprising PDGF, wherein at least 25% of the PDGF is retained in the fibrin sealant for at least 3 days.

In a related aspect, the invention provides a method for the controlled release of a PDGF protein, said protein selected from the group consisting of PDGF-AB and PDGF-BB, in a patient in need thereof, comprising administering to said patient a fibrin sealant comprising PDGF, wherein at least 20% of the PDGF is retained in the fibrin sealant for at least 10 days.

It is contemplated that the PDGF released from the fibrin sealant is biologically active.

In some embodiments, at least 35% to 90% of the PDGF is retained in the fibrin sealant for at least 3 days. In a related embodiment, at least 45% to 75% of the PDGF is retained in the fibrin sealant for at least 3 days. In a further embodiment, at least 60% of the PDGF is retained in the fibrin sealant for at least 3 days.

In another embodiment, at least 25% to 75% of the PDGF is retained in the fibrin sealant for at least 10 days. In a related embodiment, at least 45% to 55% of said PDGF is retained in the fibrin sealant for at least 10 days.

In a related embodiment, it is contemplated that the fibrin sealant may have release kinetics of the above ranges for either or both of 3 days or 10 days.

In one embodiment, the fibrin sealant is produced by combining a FC component and a thrombin component in admixture. In another embodiment, the PDGF is added to the FC component before admixture of the FC component with the thrombin component. In a further embodiment, the PDGF is added to the thrombin component.

In a related embodiment, it is contemplated that the PDGF release may decrease by a regular amount each day. For example, the PDGF amount in the fibrin sealant may decrease by about 1% a day, by about 2% a day, by about 3% a day, by about 4% a day, by about 5% a day, by about 6% a day, by about 7% a day, by about 8% a day, by about 9% a day or by about 10% a day, or the desired amount of release may be adjusted based on the FC concentration or thrombin concentration used to formulate the fibrin sealant.

The invention contemplates that the final concentration of the FC component in the sealant is within the range of about 1 mg/ml to about 150 mg/ml. It is also contemplated that, in some embodiments, the final concentration of the thrombin component in the sealant is within the range of about 1 IU/ml to 250 IU/ml. In one embodiment, the final FC concentration is about 5 mg/ml, about 10 mg ml, about 20 mg/ml or about 40 mg/ml, and the final thrombin concentration is about 2 IU/ml.

In one embodiment, the final PDGF concentration in the sealant is from about 1 ng/ml to about 1 mg/ml.

In a further embodiment, it is contemplated that the PDGF is PDGF-AB. In one embodiment, at least 60% of said PDGF-AB is retained in said fibrin sealant for at least 3 days, and wherein at least 40% of said PDGF-AB is retained in said fibrin sealant for at least 10 days. In a further embodiment, at least 80% of said PDGF-AB is retained in said fibrin sealant for at least 3 days, and wherein at least 60% of said PDGF-AB is retained in said fibrin sealant for at least 10 days.

In a related embodiment, it is contemplated that the PDGF is PDGF-BB. In one embodiment, at least 55% of said PDGF-BB is retained in said fibrin sealant for at least 3 days, and wherein at least 25% of said PDGF-BB is retained in said fibrin sealant for at least 10 days.

In a further aspect, the invention contemplates a method for treating a patient suffering from a disorder or disease which would benefit from in situ controlled release of PDGF protein, said protein selected from the group consisting of PDGF-AB or PDGF-BB, said method comprising administering to said patient a fibrin sealant comprising the PDGF protein, wherein the fibrin sealant provides a controlled release of the PDGF wherein at least 25% of the PDGF is retained in the fibrin sealant for at least 3 days, and said PDGF is released at a rate effective to treat said disorder or disease.

In a further aspect, the invention contemplates a method for treating a patient suffering from a disorder or disease which would benefit from in situ controlled release of a bioactive PDGF protein, said protein selected from the group consisting of PDGF-AB or PDGF-BB, said method comprising administering to said patient a fibrin sealant comprising the PDGF protein, wherein the fibrin sealant provides a controlled release of the PDGF wherein at least 20% of the PDGF is retained in the fibrin sealant for at least 10 days and said PDGF is released at a rate effective to treat said disorder or disease.

The invention also provides for use of a fibrin sealant comprising a PDGF protein, selected from the group consisting of PDGF-AB or PDGF-BB, in the manufacture of a medicament for treating a patient suffering from a disorder or disease which would benefit from in situ controlled release of a PDGF protein, wherein the fibrin sealant provides a controlled release of the PDGF as above.

The invention contemplates that the release kinetics described above are applicable to the method for treating a patient who would benefit from in situ controlled release of a PDGF protein, or to use of the fibrin sealant in the manufacture of a medicament to treat said patient.

In one aspect, the patient is suffering from a disease which would benefit from the controlled release of PDGF in vivo which would be apparent to one of ordinary skill in the art. In one embodiment, the disease or disorder is selected from the group consisting of a musculoskeletal disease or disorder, a soft tissue disease or disorder and a cardiovascular disease.

In one embodiment, the fibrin sealant is administered to a patient using methods well-known in the art, such as injection, spray, endoscopic administration or pre-formed gel, by itself or in combination with other materials, and other methods known to one of ordinary skill in the art.

The invention also provides a kit for preparing a fibrin sealant comprising a bioactive PDGF protein, said protein selected from the group consisting of PDGF-AB or PDGF-BB, and said fibrin sealant having a desired PDGF release rate, the kit comprising, a) a first vial or first storage container containing a FC component, wherein the vial optionally comprises a PDGF component, and b) a second vial or second storage container having a thrombin component, said kit optionally containing a third vial or third storage container having a PDGF component when said first vial or first storage container does not include a PDGF component, said kit further containing instructions for use thereof. The kit may also comprise instruments for use or administration of the fibrin sealant in vitro or in vivo.

Other features and advantages of the invention will become apparent from the following detailed description. It should be understood, however, that the detailed description and the specific examples, while indicating specific embodiments of the invention, are given by way of illustration only, because various changes and modifications within the spirit and scope of the invention will become apparent to those skilled in the art from this detailed description.

BRIEF DESCRIPTION OF THE DRAWINGS

FIG. 14C shows the graphical determination of the association and dissociation rate constants for the interaction of PDGF-AB with FC from TISSEEL VH S/D.

DETAILED DESCRIPTION OF THE INVENTION

Figure 1:
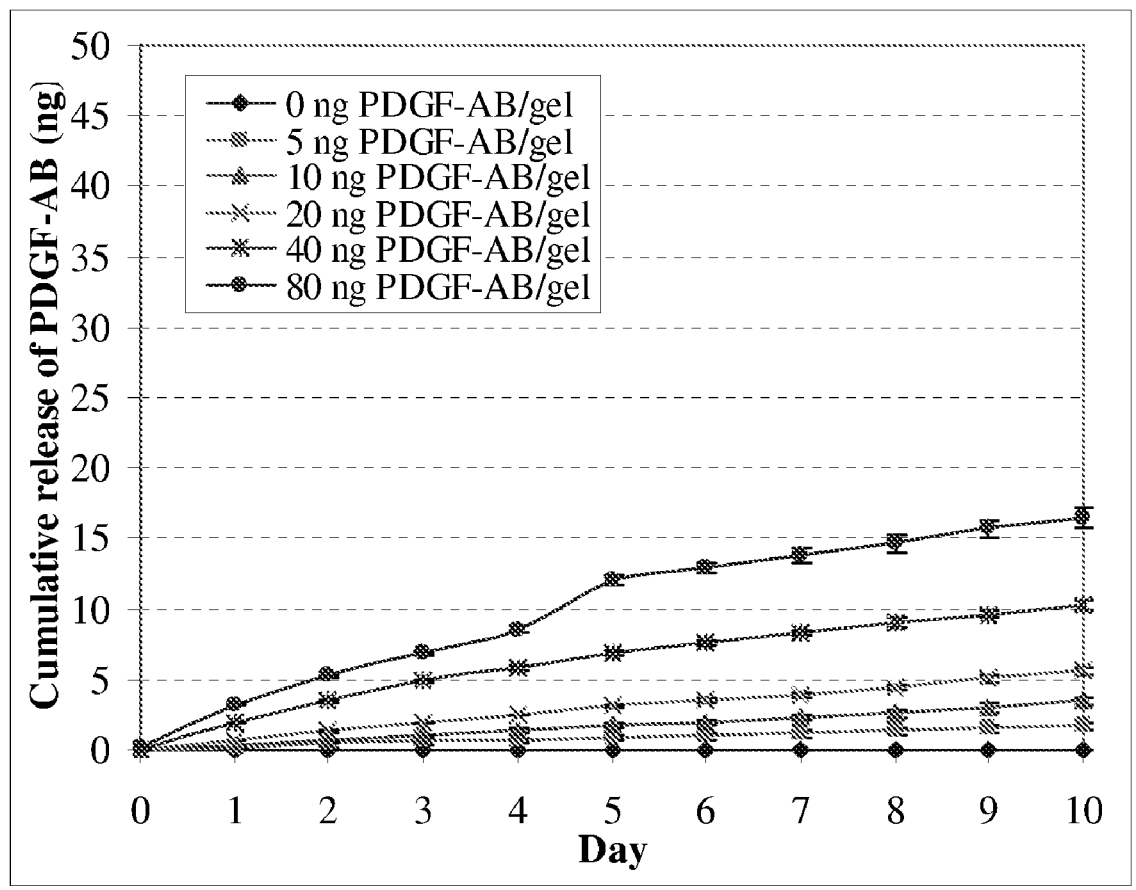
FIG. 1 shows the effects of PDGF-AB amount on its cumulative release from TISSEEL VH S/D gels ([FC]=20 mg/ml and [Thrombin]=2 IU/ml).

The invention provides a fibrin gel containing PDGF for controlled release through reversible binding in situ in therapeutic applications, including treatment of musculoskeletal diseases, soft tissue disorders, and vascular diseases. The invention contemplates that the PDGF released from the gel retains its biological activity such that release from the fibrin sealant in vitro or in vivo modulates the desired biological activity. The invention also provides a method for determining the concentration of the FC component or thrombin component useful in formulating the fibrin sealant to obtain desired PDGF release kinetics.

Unless otherwise defined, all technical and scientific terms used herein have the same meaning as commonly understood by one of ordinary skill in the art to which this invention belongs. The following references provide one of skill with a general definition of many of the terms used in this invention: Singleton, et al., DICTIONARY OF MICROBIOLOGY AND MOLECULAR BIOLOGY (2d ed. 1994); THE CAMBRIDGE DICTIONARY OF SCIENCE AND TECHNOLOGY (Walker ed., 1988); THE GLOSSARY OF GENETICS, 5TH ED., R. Rieger, et al. (eds.), Springer Verlag (1991); and Hale and Marham, THE HARPER COLLINS DICTIONARY OF BIOLOGY (1991).

Each publication, patent application, patent, and other reference cited herein is incorporated by reference in its entirety to the extent that it is not inconsistent with the present disclosure.

It is noted here that as used in this specification and the appended claims, the singular forms "a," "an," and "the" include plural reference unless the context clearly dictates otherwise.

As used herein, the following terms have the meanings ascribed to them unless specified otherwise.

As used herein the terms "fibrin sealant," "fibrin gel," "fibrin adhesive," "fibrin clot" or "fibrin matrix" are used interchangeably and refer to a three-dimensional network comprising at least a fibrinogen complex (FC) component and a thrombin component, which can act as a scaffold for cell growth and release of abioactive material over time.

As used herein the terms "controlled release" and "delayed release" have the same meaning and refer to retention of an agent (e.g., growth factor) in a fibrin gel. Controlled release is due not only to slow and steady secretion/release of the growth factor by diffusion or by dissociation of the bound growth factor and its subsequent diffusion from the gel, but is also due to the disintegration and enzymatic cleavage of the matrix.

As used herein, "in situ formation" refers to either formation at a physiological temperature and at the site of injection in the body or to formation of the fibrin sealant at appropriate in vitro conditions. This term is typically used to describe the formation of covalent linkages between precursor molecules in the fibrin sealant, which are substantially not crosslinked prior to and at the time of administration.

As used herein, "fibrinogen complex (FC) component" refers to the fibrin/fibrinogen solution which is mixed with thrombin resulting in a clot-like fibrin sealant. The FC is composed mainly of fibrinogen and fibronectin, and may also contain catalytic amounts of FXIII and plasminogen. The FC component may also be referred to as Sealer Protein.

As used herein, "thrombin component" refers to the thrombin solution which is mixed with the FC component which results in a clot-like fibrin sealant.

As used herein, "platelet derived growth factor component" or "PDGF component" refers to the addition of the growth factor in solution to the liquid form of the fibrin sealant. Each of the PDGF component, the FC complex component and the thrombin component may be added separately to form the fibrin sealant comprising PDGF. Optionally, the PDGF component is added to the liquid FC component before admixture with the thrombin component or to the thrombin component before admixture with the FC component. The PDGF component may include either PDGF-AB or PDGF-BB, or both PDGF-AB and PDGF-BB.

As used herein, "recombinant human PDGF" refers to recombinant human platelet derived growth factor (rh PDGF) obtained via recombinant DNA technology. It may be produced by any method known in the art.

As used herein the term "bioactive" or "biologically active" refers to the biological property wherein a protein, e.g., a PDGF protein, in a solution or in a fibrin sealant exhibits the same or similar biological activity when compared to a naturally expressed (i.e., when expressed either recombinantly or in vivo) protein.

As used herein a "detectable moiety," "detectable label" or "label" refers to a composition detectable by spectroscopic, photochemical, biochemical, immunochemical, or chemical means. For example, useful labels include $^{32}P$, $^{35}S$, fluorescent dyes, electron-dense reagents, enzymes (e.g., as commonly used in an ELISA), biotin-streptavidin, dioxigenin, haptens and proteins for which anti-sera or monoclonal antibodies are available, or nucleic acid molecules with a sequence complementary to a target. The detectable moiety often generates a measurable signal, such as a radioactive, chromogenic, or fluorescent signal, that can be used to quantitate the amount of bound detectable moiety in a sample.

Fibrin Sealants

Many forms of fibrin are available for use as a fibrin sealant. Fibrin gels can be synthesized from autologous plasma, cryoprecipitated plasma (e.g. fibrin glue kits, which are available commercially), fibrinogen purified from plasma, and recombinant fibrinogen and factor XIIIa. Each of these materials provides a fundamentally similar matrix, with small variations in the biochemical compositions (Sierra D H, J Biomater Appl, 7, 309-352 (1993)). Similarities between these materials exist both in specific enzymatic bioactivity and general healing responses.

The fibrin gel useful in the invention is formed from a fibrin sealant, which consists of two main components: fibrinogen complex (FC) and thrombin. The FC is composed mainly of fibrinogen and fibronectin, and may also contain catalytic amounts of FXIII and plasminogen. The FC and thrombin components are generally derived from human plasma, but may also be produced by recombinant/genetic engineering techniques. Examples of Fibrin Sealants are described in U.S. Pat. Nos. 5,716,645; 5,962,405; 6,579,537 and include TISSEEL VH and TISSEEL VH S/D (Baxter AG, Vienna, Austria).

To form the fibrin gel, the FC is first reconstituted, thawed or otherwise prepared according to package instructions, further diluted as needed using dilution buffers and therapeutic agent is added to the liquid FC. Alternatively, the therapeutic agent can be added in the thrombin component. Most commercially available fibrin sealants include an inhibitor of gel lysis such as aprotinin, which can be added to the FC at the discretion of the user. A description of aprotinin and other gel lysis inhibitors is provided in WO 99/11301. The thrombin component is also reconstituted to liquid form using $CaCl_2$ solution, further diluted as needed using dilution buffers. It is contemplated that the thrombin component is mixed with the FC component further comprising a PDGF to form the fibrin gel. Fibrin sealants have also been designed which lack the aprotinin ingredient (EVICEL, Ethicon, Inc, New Jersey).

Additional methods for producing fibrinogen-containing preparations that can be used as tissue adhesives include production from cryoprecipitate, optionally with further washing and precipitation steps with ethanol, ammonium sulphate, polyethylene glycol, glycine or beta-alanine, and production from plasma within the scope of the known plasma fractionation methods, respectively (cf., e.g., "Methods of plasma protein fractionation", 1980, ed.: Curling, Academic Press, pp. 3-15, 33-36 and 57-74, or Blomb ck B. and M., "Purification of human and bovine fibrinogen", Arkiv Kemi 10, 1959, p. 415f.). Fibrin sealant may also be made using a patient own blood plasma. For example, the CRYOSEAL (Thermogenesis Corp., Rancho Cordova, Calif.) or VIVOSTAT (Vivolution A/S, Denmark) fibrin sealant systems enable the production of autologous fibrin sealant components from a patient's blood plasma. The components of Fibrin Sealants are available in lyophilized, deep-frozen liquid, or liquid form.

The components of the fibrin gel are added at appropriate concentrations to provide the type of controlled release desired. The FC component may be added in varying concentrations, including but not limited to 5 mg/ml, 10 mg/ml, 15 mg/ml, 20 mg/ml, 25 mg/ml, 30 mg/ml, 35 mg/ml, 40 mg/ml, 45 mg/ml, 50 mg/ml, up to 150 mg/ml (final concentrations in the gels), or in intermediate concentrations as necessary. Further, the concentration of FC component may be combined with any appropriate concentration of thrombin component, including, but not limited to 1 IU/ml, 2 IU/ml, 5 IU/ml, 7 IU/ml, 10 IU/ml, 15 IU/ml, 20 IU/ml, 25 IU/ml, 30 IU/ml, 35 IU/ml, 40 IU/ml, 50 IU/ml, 60 IU/ml, 70 IU/ml, 80 IU/ml, 90 IU/ml, 100 IU/ml, 125 IU/ml, 150 IU/ml, 175 IU/ml, 200 IU/ml, 225 IU/ml and 250 IU/ml, or in intermediate concentrations as necessary.

It is contemplated that an agent such as PDGF is added to the fibrin sealant composition in order to make a controlled release system for the therapeutic agent. The PDGF may be added in any concentration that provides an adequate delayed release formulation, within a range of 1 ng/ml to 1 mg/mL of PDGF. Exemplary concentrations of PDGF in the fibrin sealant include, but are not limited to 1 ng/ml, 5 ng/ml, 10 ng/ml, 15 ng/ml, 20 ng/ml, 40 ng/ml, 50 ng ml, 100 ng/ml, 250 ng/ml, 500 ng/ml, 1 µg/ml, 5 µg/ml, 10 µg/ml, 25 µg/ml, 50 µg/ml, 100 µg/ml, 250 µg/ml, 500 µg/ml, 750 µg/ml and 1 mg/ml.

It is contemplated that the concentration of FC or thrombin used in the fibrin sealant are such that the PDGF added in the fibrin gel is released in a therapeutically effective amount over the course of several days to weeks. In one aspect, the PDGF is released from the fibrin gel for 1 day, 2 days, 3 days, 4 days, 5 days, 6 days, 7 days, 8 days, 9 days, 10 days, 11 days, 12 days, 13 days, 14 days, 15 days, 16 days, 17 days 18 days, 19 days, 20 days, or longer.

The PDGF is released form the fibrin sealant in a controlled or delayed release manner, such that the PDGF is available in situ over a sustained period of time. It is contemplated that the PDGF release may decrease by a regular amount each day, for example, the PDGF levels may decrease by about 1% a day, by about 2% a day, by about 3% a day, by about 4% a day, by about 5% a day, by about 6% a day, by about 7% a day, by about 8% a day, by about 9% a day or by about 10% a day or more.

In a related embodiment, it is contemplated that at least 25% of the PDGF is retained in the fibrin gel for at least 3 days. In a further embodiment, at least 35% to 90%, at least 45% to 75%, or at least 60% of the PDGF is retained in the fibrin gel for at least 3 days. It is further contemplated that at least 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, or 90% of the PDGF is retained in the fibrin gel for at least 3 days.

In another embodiment, at least 20% of the PDGF is retained in the fibrin gel for at least 10 days. In a further embodiment, at least 25% to 75% or 45% to 55% of the PDGF is retained for at least 10 days. It is further contemplated that at least 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74% or 75% of the PDGF is retained in the fibrin gel for at least 10 days.

The invention provides a method to formulate a fibrin sealant having desired release kinetics by modifying the concentration of the components of the fibrin sealants. In one aspect, the method contemplates determining the amount of PDGF released from a first fibrin sealant having a known initial amount of PDGF and a known final concentration of FC, modifying the known final concentration of FC used in the first fibrin sealant in of step (a) to produce a second fibrin sealant, wherein increasing or decreasing the concentration of FC in the second sealant compared to the known final concentration of FC in the first sealant adjusts the rate of PDGF release from the second sealant as compared to the release of PDGF from the first sealant of step, and wherein the second sealant has the same initial amount of PDGF as the first sealant in step.

In one embodiment, the final FC concentration in the first or second sealant is within the range of about 1 mg/ml to about 150 mg/ml. In a related embodiment, the FC concentration of the first fibrin sealant differs from the final FC concentration in the second sealant by about 1 mg/ml to about 149 mg/ml, by about 5 mg/ml to about 75 mg/ml, or by about 10 mg/ml to about 60 mg/ml. In a further embodiment, the final FC concentration of the first fibrin sealant differs from the final FC concentration in the second sealant by about 1 mg/ml, 2 mg/ml, 3 mg/ml, 4 mg/ml, 5 mg/ml, 10 mg/ml, 15 mg/ml, 20 mg/ml, 25 mg/ml, 30 mg/ml, 35 mg/ml 40 mg/ml, 45 mg/ml, 50 mg/ml, or any amount between these concentrations, up to about 149 mg/ml.

It is contemplated that the fibrin sealant useful in the invention may be combined with additional materials or agents for purposes of in vitro or in vivo use. Such agents include additional therapeutic agents, including, but not limited to, growth factors, cytokines, chemokines, a blood clotting factor, an enzyme, a chemokine, a soluble cell-surface receptor, a cell adhesion molecule, an antibody, a hormone, a cytoskeletal protein, a matrix protein, a chaperone protein, a structural protein, a metabolic protein, and others known in the art (See, for example, Physicians Desk Reference, 62$^{nd}$ Edition, 2008, Thomson Healthcare, Montvale, N.J.).

Additional materials useful in the fibrin sealant include materials that could be combined with the sealant for musculoskeletal diseases which may be load bearing materials, including but not limited to, polymers, coral, ceramics, glass, metals, bone-derived materials, hydroxyapatite, synthetic scaffolds materials, combinations of these materials, and other materials known in the art (See, e.g., Guehennec et al., (European Cells and Materials, 8:1-11, 2004), U.S. Pat. Nos. 7,122,057 and 6,696,073).

In one embodiment, the fibrin gels can be used as a carrier system to deliver biologically active PDGF after reversible binding and in a controlled manner by adjusting the concentrations of FC and thrombin.

In one embodiment of the invention, when the fibrin gels are made of TISSEEL Vapor Heated Solvent/Detergent (TISSEEL VH S/D) using FC at 5 mg/ml and Thrombin at 2 IU/ml (final concentrations in the gels), at least about 65% of the added PDGF-BB (15 ng) is retained in the gels after 3 days. In another embodiment of the invention, when the fibrin gels are made of TISSEEL VH S/D using FC at 40 mg/ml and Thrombin at 2 IU/ml (final concentrations in the gels), at least about 85% of the added PDGF-BB (15 ng) is retained in the gels after 3 days. Therefore, the retention of PDGF-BB increases with higher FC concentrations when using fibrin gels made of TISSEEL VH S/D.

In another embodiment of the invention, when the fibrin gels are made of TISSEEL VH of different lot numbers, using FC at 20 mg/ml and Thrombin at 2 IU/ml (final concentrations in the gels), at least about 70% of PDGF-BB is retained in the gels from one lot after 10 days, about 60% from a second lot and about 40% from a third lot. One difference between these lots is the Factor XIII content (42.2 U/ml, 33.9 U/ml and <1 U/ml, respectively). In another embodiment of the invention, when the fibrin gels are made of TISSEEL VH S/D of different lot numbers, using FC at 20 mg/ml and Thrombin at 2 IU/ml (final concentrations in the gels), at least about 60% of PDGF-BB is retained in the gels from all lots after 10 days. For PDGF-AB release, at least about 75% was retained by day 10 in two of the three lots, and about 68% growth factor was retained in the third lot at 10 days.

It will be understood to one of ordinary skill in the art that the embodiments set out above are exemplary embodiments of PDGF release from a commercially available fibrin sealant and are not meant to limit the invention in any way.

PDGF Protein

Platelet-Derived Growth Factor (PDGF) is secreted by platelets during the early phases of wound and fracture healing. It has been shown to stimulate the migration of osteoblasts and mesenchymal progenitor cells (Mehrotra et al., J Cell Biochem 93:741-52, 2004; Fiedler et al., J Cell Biochem 93:990-98, 2004), but its role in fracture healing and bone repair has not been clearly defined. PDGF also regulates different aspects of angiogenesis, which itself is also critical during bone growth. PDGF also plays a role in stimulating angiogenesis, which is a fundamental process required for normal growth and development of tissues, and involves the proliferation of new capillaries from pre-existing blood vessels. Increasing the rate of angiogenesis is useful in certain disorder such as those associated with decreased tissue perfusion, such as coronary artery and peripheral vascular disease, to name a few.

PDGF-A (Genbank Accession No. NP_002598) and PDGF-B ((Genbank Accession No. NP_002599) can homodimerize or heterodimerize to produce three different isoforms: PDGF-AA, PDGF-AB, or PDGF-BB. PDGF-A is only able to bind the PDGF α-receptor (PDGFR-α including PDGFR-α/α homodimers). PDGF-B can bind both the PDGFR-α and a second PDGF receptor (PDGFR-β). More specifically, PDGF-B can bind to PDGFR-α/α and PDGFR-β/β homodimers, as well as PDGFR-α/β heterodimers.

PDGF-AA and -BB are the major mitogens and chemoattractants for cells of mesenchymal origin, but have no or little effect on cells of endothelial lineage, although both PDGFR-α and -β are expressed on endothelial cells (EC). PDGF-AB and PDGF-BB have been shown to be involved in the stabilization/maturation of newly formed vessels (Isner et al., Nature 415:234-9, 2002; Vale et al., J Interv Cardiol 14:511-28, 2001); Heldin et al., Physiol Rev 79:1283-1316, 1999; Betsholtz et al., Bioessays 23:494-507, 2001). Other data however, showed that PDGF-AA and PDGF-BB inhibited bFGF-induced angiogenesis in vivo via PDGFR-α signaling. PDGF-AA is among the most potent stimuli of mesenchymal cell migration, but it either does not stimulate or it minimally stimulates EC migration. In certain conditions, PDGF-AA even inhibits EC migration (Thommen et al., J Cell Biochem. 64:403-13, 1997; De Marchis et al., Blood 99:2045-53, 2002; Cao et al., FASEB. J. 16:1575-83, 2002). Moreover, PDGFR-α has been shown to antagonize the PDGFR-β-induced SMC migration Yu et al. (Biochem. Biophys. Res. Commun. 282:697-700, 2001) and neutralizing antibodies against PDGF-AA enhance smooth muscle cell (SMC) migration (Palumbo, R., et al., Arterioscler. Thromb. Vasc. Biol. 22:405-11, 2002). Thus, the angiogenic/arteriogenic activity of PDGF-A and -B, especially when signaling through PDGFR-α, has been controversial.

PDGF-AA and -BB have been reported to play important roles in the proliferation and differentiation of both cardiovascular and neural stem/progenitor cells. PDGF-AA stimulated oligodendrocyte precursor proliferation through αvβ3 integrins (Baron, et al., Embo. J. 21:1957-66, 2002) while PDGF-BB induced differentiation of Flk1+ embryonic stem cells into vascular mural cells (Carmeliet, P., Nature 408:43-45, 2000; Yamashita et al., Nature 408:92-6, 2000), and potently increased neurosphere derived neuron survival (Caldwell et al., Nat Biotechnol. 19:475-479, 2001).

PDGF protein has been used in formulation of fibrin gel with mixed success. Thomopoulous et al. (J Orth Res 25:1358-68, 2007) prepared a fibrin gel comprising fibrinogen, thrombin, a peptide component and heparin and further added PDGF-BB in varying concentrations to determine the passive release kinetics of the growth factor. The study showed that release of the growth factor was dependent on the amount of heparin in the fibrin gel. PDGF has also been detected in fibrin gels comprising plasma platelet T preparations (see for example, Yazawa et al., J Craniofac Surg 15:439-46, 2004), and used to stimulate embryonic stem cells in a fibrin scaffold (Willerth et al., Stem Cells. 25:2235-2244, 2007).

The PDGF molecules useful for the present invention include the full-length protein, precursors of the protein, subunits or fragments of the protein, and functional derivatives thereof. Reference to PDGF is meant to include all potential forms of such proteins, including naturally-derived protein preparations.

According to the present invention, the term recombinant PDGF does not underlie a specific restriction and may include any PDGF, heterologous or naturally occurring, obtained via recombinant DNA technology, or a biologically active derivative thereof. In certain embodiments, the term encompasses proteins and nucleic acids, e.g., gene, pre-mRNA, mRNA, and polypeptides, polymorphic variants, alleles, mutants, and interspecies homologs that: (1) have an amino acid sequence that has greater than about 60% amino acid sequence identity, 65%, 70%, 75%, 80%, 85%, 90%, 91%, 92%, 93%, 94%, 95%, 96%, 97%, 98% or 99% or greater amino acid sequence identity, over a region of at least about 25, 50, 100, 150, 200, or more amino acids, to a PDGF-AB or PDGF-BB polypeptide encoded by a referenced nucleic acid or an amino acid sequence described herein; (2) specifically bind to antibodies, e.g., polyclonal antibodies, raised against an immunogen comprising a referenced amino acid sequence as described herein immunogenic fragments thereof, and conservatively modified variants thereof; (3) specifically hybridize under stringent hybridization conditions to a nucleic acid encoding a referenced amino acid sequence as described herein, and conservatively modified variants thereof; (4) have a nucleic acid sequence that has greater than about 95%, greater than about 96%, 97%, 98%, 99%, or higher nucleotide sequence identity, over a region of at least about 25, 50, 100, 150, 200, 250, 500, 1000, 1500, 2000 or more nucleotides (up to the full length sequence of nucleotides of the mature protein), to a reference nucleic acid sequence as described herein.

A polynucleotide or polypeptide sequence is typically from a mammal including, but not limited to, primate, e.g., human; rodent, e.g., rat, mouse, hamster; cow, pig, horse, sheep, or any other mammal. The nucleic acids and proteins of the invention can be recombinant molecules (e.g., heterologous and encoding the wild type sequence or a variant thereof, or non-naturally occurring). For the structure of human PDGF refer to Genbank Database maintained by the National Center for Biotechnology Information (NCBI): Human PDGF-A (Genbank Accession No. NP_002598, NM_002607.4) and PDGF-B (Genbank Accession No. NP_002599, NM_002608). PDGF-AB and PDGF-BB are homo- or hetero-dimers of the PDGF-A and PDGF-B sequences.

The production of PDGF may include any method known in the art for (i) the production of recombinant DNA by genetic engineering, e.g. via reverse transcription of RNA and/or amplification of DNA, (ii) introducing recombinant DNA into prokaryotic or eukaryotic cells by transfection, e.g. via electroporation or microinjection, (iii) cultivating said transformed cells, e.g. in a continuous or batchwise manner, (iv) expressing PDGF, e.g. constitutively or upon induction, and (v) isolating said PDGF, e.g. from the culture medium or by harvesting the transformed cells, in order to obtain purified PDGF, e.g. via anion exchange chromatography or affinity chromatography.

The PDGF can be produced by expression in a suitable prokaryotic or eukaryotic host system characterized by producing a pharmacologically acceptable PDGF molecule. Commonly used host cells include: Prokaryotic cells such as gram negative or gram positive bacteria, i.e., any strain of *E. coli, Bacillus, Streptomyces, Saccharomyces, Salmonella*, and the like. Examples of eukaryotic cells are insect cells such as D. MeI-2, Sf4, Sf5, Sf9, and Sf21 and High 5; plant cells and various yeast cells such as *Saccharomyces* and *Pichia*; mammalian cells, such as CHO (Chinese hamster ovary) cells; baby hamster kidney (BHK) cells; human kidney 293 cells; COS-7 cells, HEK 293, SK-Hep, and HepG2, and others known in the art. There is no limitation to the reagents or conditions used for producing or isolating PDGF according to the present invention, and any system known in the art or commercially available can be employed. In a preferred embodiment of the present invention, PDGF is obtained by methods as described in the state of the art.

A wide variety of vectors can be used for the preparation of the PDGF and can be selected from eukaryotic and prokaryotic expression vectors well-known in the art. Examples of vectors for prokaryotic expression include, but are not limited to, plasmids such as pRSET, pET, pBAD, etc., wherein the promoters used in prokaryotic expression vectors include lac, trc, trp, recA, araBAD, etc. Examples of vectors for eukaryotic expression include, butr are not limited to: (i) for expression in yeast, vectors such as pAO, pPIC, pYES, pMET, using promoters such as AOX1, GAP, GAL1, AUG1, etc; (ii) for expression in insect cells, vectors such as pMT, pAc5, pIB, pMIB, pBAC, etc., using promoters such as PH, p10, MT, Ac5, OpIE2, gp64, polh, etc., and (iii) for expression in mammalian cells, vectors such as pSVL, pCMV, pRc/RSV, pcDNA3, pBPV, etc., and vectors derived from viral systems such as vaccinia virus, adeno-associated viruses, herpes viruses, retroviruses, etc., using promoters such as CMV, SV40, EF-1, UbC, RSV, ADV, BPV, and β-actin.

Host cells containing the polypeptide-encoding DNA or RNA are cultured under conditions appropriate for growth of the cells and expression of the DNA or RNA. Those cells which express the polypeptide can be identified, using known methods, and the recombinant protein isolated and purified, using known methods; either with or without amplification of polypeptide production. Identification can be carried out, for example, through screening genetically modified mammalian cells displaying a phenotype indicative of the presence of DNA or RNA encoding the protein, such as PCR screening, screening by Southern blot analysis, or screening for the expression of the protein. Selection of cells having incorporated protein-encoding DNA may be accomplished by including a selectable marker in the DNA construct and culturing transfected or infected cells containing a selectable marker gene under conditions appropriate for survival of only those cells that express the selectable marker gene. Further amplification of the introduced DNA construct can be affected by culturing genetically modified cells under conditions appropriate for amplification (e.g., culturing genetically modified cells containing an amplifiable marker gene in the presence of a concentration of a drug at which only cells containing multiple copies of the amplifiable marker gene can survive).

In one embodiment of the invention, the biological activity of the released PDGF from fibrin gels was tested. The change of Human Mesenchymal Stem Cell (HMSC) morphology into a more elongated shape after culture in monolayers in medium supernatants from gels with added PDGF (i.e., in medium containing released PDGF-BB) and a tendency to increase cell proliferation indicated the biological activity of the released growth factor.

Methods of Determining Protein Concentration in a Sample.

Therapeutic proteins are often difficult to detect in serum samples due to their similarity to the endogenously produced, naturally-occurring protein. However, it is often beneficial to determine the amount of a therapeutic polypeptide, fragment, variant or analog thereof that has been administered to assess whether the therapeutic protein exhibits desired characteristics such as greater solubility or stability, resistance to enzyme digestion, improved biological half-life, and other features known to those skilled in the art. The method also allows for detection of authorized uses of therapeutic proteins which may be protected by intellectual property rights.

The present invention uses a method to detect the release of PDGF from a fibrin gel containing PDGF and determine the release kinetics of the protein. The comparison of these release kinetics from fibrin sealants made using varying concentrations of FC component helps to determine the desired release rate for the therapeutic purpose. The ability to identify the amount of protein released from the fibrin sealant over time aids in determination of the optimal therapeutic based on half-life, absorption, stability, etc. The detection assay may be an enzyme linked immunosorbant assay (ELISA), a radioimmunoassay (RIA), a scintillation proximity assay (SPA), surface plasma resonance (SPR), or other binding assays known in the art.

Generally, for detecting the presence of PDGF in a sample, the PDGF is bound to a PDGF binding agent, such as an antibody, soluble receptor or other protein or agent which binds PDGF.

For the detection step or testing of biological activity, the PDGF protein may be linked to a detectable moiety or a detectable label. Detectable moiety or label refers to a composition detectable by spectroscopic, photochemical, biochemical, immunochemical, or chemical means. The detectable moiety often generates a measurable signal, such as a radioactive, chromogenic, or fluorescent signal, that can be used to quantitate the amount of bound detectable moiety in a sample. The detectable moiety can be incorporated in or attached to the protein either covalently, or through ionic, van der Waals or hydrogen bonds, e.g., incorporation of radioactive nucleotides, or biotinylated nucleotides that are recognized by streptavidin. The detectable moiety may be directly or indirectly detectable. Indirect detection can involve the binding of a second directly or indirectly detectable moiety to the detectable moiety. For example, the detectable moiety can be the ligand of a binding partner, such as biotin, which is a binding partner for streptavidin. The binding partner may itself be directly detectable, for example, an antibody may be labeled with a fluorescent molecule. Selection of a method quantitation of the signal is achieved by, e.g., scintillation counting, densitometry, or flow cytometry.

Examples of labels suitable for use in the assay methods of the invention include, radioactive labels, fluorophores, electron-dense reagents, enzymes (e.g., as commonly used in an ELISA), biotin, digoxigenin, or haptens as well as proteins which can be made detectable, e.g., by incorporating a radiolabel into the hapten or peptide, or used to detect antibodies specifically reactive with the hapten or peptide. Also contemplated are proteins for which antisera or monoclonal antibodies are available, or nucleic acid molecules with a sequence complementary to a target, a nanotag, a molecular mass bead, a magnetic agent, a nano- or micro-bead containing a fluorescent dye, a quantum dot, a quantum bead, a fluorescent protein, dendrimers with a fluorescent label, a micro-transponder, an electron donor molecule or molecular structure, or a light reflecting particle.

Additional labels contemplated for use with present invention include, but are not limited to, fluorescent dyes (e.g., fluorescein isothiocyanate, Texas red, rhodamine, and the like), radiolabels (e.g., $^3$H, $^{125}$I, $^{35}$S, $^{14}$C, or $^{32}$P), enzymes (e.g., horse radish peroxidase, and others commonly used in an ELISA), and colorimetric labels such as colloidal gold, colored glass or plastic beads (e.g., polystyrene, polypropylene, latex, etc.), and luminescent or chemiluminescent labels (e.g., Europium (Eu), MSD Sulfo-Tag).

The label may be coupled directly or indirectly to the desired component of the assay according to methods well known in the art. In a specific embodiment, the label is covalently bound to the component using an isocyanate or N-hydroxysuccinimide ester reagent for conjugation of an active agent according to the invention. In one aspect of the invention, bifunctional isocyanate reagents are used to conjugate a label to a biopolymer to form a label biopolymer conjugate without an active agent attached thereto. The label biopolymer conjugate may be used as an intermediate for the synthesis of a labeled conjugate according to the invention or may be used to detect the biopolymer conjugate. As indicated above, a wide variety of labels can be used, with the choice of label depending on sensitivity required, ease of conjugation with the desired component of the assay, stability requirements, available instrumentation, and disposal provisions. Non-radioactive labels are often attached by indirect means. Generally, a ligand molecule (e.g., biotin) is covalently bound to the molecule. The ligand then binds to another molecules (e.g., streptavidin) molecule, which is either inherently detectable or covalently bound to a signal system, such as a detectable enzyme, a fluorescent compound, or a chemiluminescent compound.

The compounds useful in the method of the invention can also be conjugated directly to signal-generating compounds, e.g., by conjugation with an enzyme or fluorophore. Enzymes suitable for use as labels include, but are not limited to, hydrolases, particularly phosphatases, esterases and glycosidases, or oxidotases, particularly peroxidases. Fluorescent compounds suitable for use as labels include, but are not limited to, those listed above as well as fluorescein derivatives, rhodamine and its derivatives, dansyl, umbelliferone, eosin, TRITC-amine, quinine, fluorescein W, acridine yellow, lissamine rhodamine, B sulfonyl chloride erythroscein, ruthenium (tris, bipyridinium), europium, Texas Red, nicotinamide adenine dinucleotide, flavin adenine dinucleotide, etc. Chemiluminescent compounds suitable for use as labels include, but are not limited to, MSD Sulfa-TAG, Europium (Eu), Samarium (Sm), luciferin and 2,3-dihydrophthalazinediones, e.g., luminol. For a review of various labeling or signal producing systems that can be used in the methods of the present invention, see U.S. Pat. No. 4,391,904.

Means for detecting labels are well known to those of skill in the art and are dictated by the type of label to be detected. Thus, for example, where the label is radioactive, means for detection include a scintillation counter (e.g., radioimmunoassay, scintillation proximity assay) (Pitas et al., Drug Metab Dispos. 34:906-12, 2006) or photographic film, as in autoradiography. Where the label is a fluorescent label, it may be detected by exciting the fluorochrome with the appropriate wavelength of light and detecting the resulting fluorescence (e.g., ELISA, flow cytometry, or other methods known in the art). The fluorescence may be detected visually, by the use of electronic detectors such as charge coupled devices (CCDs) or photomultipliers and the like. Similarly, enzymatic labels may be detected by providing the appropriate substrates for the enzyme and detecting the resulting reaction product. Colorimetric or chemiluminescent labels may be detected simply by observing the color associated with the label. Other labeling and detection systems suitable for use in the methods of the present invention will be readily apparent to those of skill in the art. Such labeled modulators and ligands can be used in the diagnosis of a disease or health condition.

The method optionally includes at least one or more washing steps, wherein the bound PDGF composition is washed prior to measuring protein binding to reduce background measurements caused by unbound polypeptides. Washing of the PDGF after incubation of the polypeptide composition and before detection of PDGF is performed in appropriate buffer plus detergent. Suitable detergents include, but are not limited to alkyldimethylamine oxides, alkyl glucosides, alkyl maltosides, alkyl sulfates (such as sodium dodecyl sulfate (SDS)), NP-40, alkyl thioglucosides, betaines, bile acids, CHAP series, digitonin, glucamides, lecithins/lysolecithins, nonionic polyoxyethylene-based detergents, including TRITON-X, polysorbates, such as TWEEN® 20 and TWEEN® 80, BRIJ®, GENAPOL® and THESIT®, quaternary ammonium compounds, and the like. See also Current Protocols in Protein Science, Appendix 1B, Suppl. 11, 1998, John Wiley and Sons, Hoboken, N.J. Suitable detergents can be determined using routine experimentation (see Neugebauer, J., A Guide to the Properties and Use of Detergents in Biology and Biochemistry, Calbiochem-Novabiochem Corp., La Jolla, Calif., 1988).

Methods of Administering the Fibrin Sealant

It is contemplated that the fibrin sealant useful in the invention is administered to a subject using techniques well-known in the art, for example by injection or spray at the desired site, endoscopically, using a sponge-like carrier, pre-formed sealant or other methods known in the art. In one embodiment, the sealant is injected or sprayed and allowed to form a gel in situ.

These fibrin sealants are contemplated for administration to subjects who would benefit from the sustained/controlled release of PDGF in vivo, as would be apparent to one of ordinary skill in the art, including but not limited to the conditions set out below. In one embodiment, the patient is suffering from a musculoskeletal disease, including, but not limited to, diseases of the bones and cartilage, muscles, associated ligaments, and other connective tissues; a soft tissue disease or disorder, including but not limited to disorders affecting, muscles, fibrous tissues, fat, blood vessels, and synovial tissues; or a vascular disease.

In one embodiment, the fibrin sealants serve as a replacement for bone grafts, and thus may be applied in many of the same indications, including, but not limited to, spinal fusion cages, healing of non-union defects, bone augmentation, bone fracture repair acceleration, bone tissue reconstruction, and dental regeneration. Additionally, in another embodiment, the sealants can be used in implant integration. In implant integration, implants can be coated with a fibrin sealant inducing the neighboring bone area to grow into the surface of the implant and preventing loosening and other associated problems. In another embodiment, growth factor-enriched matrices can be used for healing chronic wounds in skin.

Additional bone or cartilage disorders or conditions include, but are not limited to, osteoarthritis, osteoporosis, osteodystrophy, rickets, osteomalacia, McCune-Albright syndrome, Albers-Schonberg disease, Paget's disease, rheumatoid arthritis, osteoarthritis, cartilage damage, periprosthetic osteolysis, osteogenesis imperfecta, metastatic bone disease, osteochondroma, osteogenesis, osteomyelitis, osteopathy, osteopetrosis, osteoschlerosis, polychondritis, articular cartilage injuries, chondrocalcinosis, chondrodysplasias, chondromalacia patella, chondrosarcoma, costochondritis, enchondroma, hallux rigidus, meniscus injuries, hip labral tear, osteochondritis dissecans (ocd), relapsing polychondritis or any condition that benefits from stimulation of bone or cartilage formation.

The fibrin sealant comprising a PDGF protein is also useful to treat vascular diseases or conditions that would benefit from increased angiogenesis and vascular growth, including but not limited to, ischemia/reperfusion, myocardial infarction, congestive heart failure, atherosclerosis, hypertension, restenosis, coronary artery disease (CAD), stroke, vessel or heart calcification, thrombosis, peripheral vascular disease, vascular wall remodeling, ventricular remodeling, rapid ventricular pacing, coronary microembolism, pressure overload, aortic bending, coronary artery ligation, vascular heart disease, valvular disease, including but not limited to, valvular degeneration caused by calcification, rheumatic heart disease, endocarditis, or complications of artificial valves; angina, heart failure, hypertension, atrial fibrillation, pericardial disease, including but not limited to, pericardial effusion and pericarditis; cardiomyopathies cardiac hypertrophy or cardiovascular developmental disorders.

Kits

Kits are also contemplated within the scope of the invention. A typical kit can comprise a fibrin sealant comprising an FC and a thrombin component. In one embodiment, the kit further comprises a PDGF protein for incorporation into the fibrin sealant. In one aspect, each component may be included in its own separate storage container, vial or vessel. In a related aspect, the PDGF may be in admixture with the FC component, and the thrombin component may be in a separate storage container. In a related aspect, the PDGF may be in admixture with the thrombin component, and the FC component may be in a separate storage container. In a related embodiment, the storage container is a vial, a bottle, a bag, a reservoir, tube, blister, pouch, patch or the like. One or more of the constituents of the formulation may be lyophilized, freeze-dried, spray freeze-dried, or in any other reconstitutable form. Various reconstitution media can further be provided if desired.

The components of the kit may be in either frozen, liquid or lyophilized form. It is further contemplated that the kit contains suitable devices for administering the fibrin gel to a subject. In a further embodiment, the kit also contains instructions for preparing and administering the fibrin sealant.

Additional aspects and details of the invention will be apparent from the following examples, which are intended to be illustrative rather than limiting.

EXAMPLES

Example 1

Materials and Methods

Release Kinetics:

The effects of recombinant (rh)-PDGF (R&D Systems) concentration on the release kinetics were analyzed using a single formulation ([FC]=20 mg/ml and [Thrombin]=2 IU/ml) of Fibrin Sealant (TISSEEL VH S/D, S/D being an added virus inactivation step to provide added safety; Baxter AG, Vienna, Austria). Different amounts of recombinant human PDGF-AB or BB were analyzed (5 ng, 10 ng, 20 ng, 40 ng, and 80 ng for 0.3 ml gels). PDGF was resuspended in the FC component at the time of the gel preparation.

The effects of FC concentrations on the release kinetics of PDGF-AB and PDGF-BB (fixed at 15 ng/0.3 ml gel) initially resuspended in the FC component of fibrin were analyzed. Four different formulations of fibrin gels (TISSEEL VH S/D) were prepared using different concentrations of FC, from 5-40 mg/ml (final concentrations in the gels) with a fixed concentration of Thrombin (2 IU/ml).

The release kinetics of PDGF-AB and BB (fixed at 15 ng/0.3 ml gel, i.e., 50 ng/ml of gel) were compared for three different Fibrin Sealant product lots of TISSEEL VH S/D using a single gel formulation ([FC]=20 mg/ml and [Thrombin]=2 IU/ml, final concentrations in the gels) to analyze any variability in the release kinetics depending on Fibrin Sealant product lot.

Release kinetics of PDGF-BB from TISSEEL VH (effects of PDGF-BB concentration, effects of FC concentration, and variability depending on Fibrin Sealant product lots) were analyzed to observe potential differences when using TISSEEL VH and TISSEEL VH S/D.

For all the experiments with TISSEEL VH S/D, gels were prepared in polypropylene Eppendorf tubes, whereas for the experiments with TISSEEL VH, gels were prepared in 24-well-polystyrene-culture plates. In all cases, gels were incubated for up to 10 days with standard Human MSC (HMSC) growth medium (Lonza Walkersville Inc., Walkersville, Md.) at 37° C. in 5% $CO_2$. Culture medium was changed every day and culture medium samples were frozen until tested for the amount of PDGF by ELISA (R&D Systems, Minneapolis, Minn.). For the experiments that evaluated the effects of FC concentration and lot-to-lot variation with TISSEEL VH S/D, gels were dissolved after the 10-day release using urokinase (1 U/ml) in complete medium. The amount of PDGF in the resulting solutions was tested in order to verify the full recovery of the amount of growth factor initially added in the gels.

Biological Activity:

Effects of Released PDGF on HMSC Monolayers:

One fibrin formulation of TISSEEL VH S/D (20 mg/ml of FC and 2 IU/ml Thrombin, final concentrations in the gels) was used to analyze the biological activity of the released PDGF from the gels (120 ng of PDGF-AB and 60 ng of PDGF-BB were added in the FC component before polymerization for gels with added PDGF). Medium supernatants collected from gels at day 3 (without changing the medium every day) were used as culture medium for HMSC monolayers. First, HMSC were pre-seeded at 2500 cells/cm$^2$ in 12 well-culture-plates (10,000 cells/well) and incubated for 4 to 5 h at 37° C. in 5% $CO_2$ to allow adherence. Then, cell culture medium was removed and replaced with medium supernatants from the gels. Some of the gels were prepared without added PDGF for control samples in order to insure that any changes observed with medium from gels with added PDGF were indeed induced by the released PDGF and not by some other potential bioactive components that could have been released from the gels themselves. Wells containing freshly prepared medium with the addition of 30 ng (15 ng/ml) of rh-PDGF were used as a positive control. The addition of 30 ng of PDGF for the positive control was based on the approximate amount of PDGF found to be released from the gels at day 3 when adding 120 ng of PDGF-AB or 60 ng of PDGF-BB in the gels at the formulation used for the experiments, and therefore, should mimic closely the tested condition, i.e., medium supernatants from gels at day 3, containing released PDGF-AB or PDGF-BB.

Analysis of cell proliferation and changes in cell morphology: Cell proliferation and morphology changes were analyzed at days 1, 4 and 7. Cell culture medium was discarded and cells were stained with a Live/Dead dye solution containing Calcein-AM and Ethidium Homodimer-1 (Sigma-Aldrich Inc., St. Louis, Mo.). Proliferation of the cells incubated with medium supernatants from gels that contained added PDGF was compared to the proliferation of cells incubated with supernatants from gels without added PDGF and to the proliferation of cells incubated with freshly prepared medium with the addition of 30 ng of PDGF (positive control). Cell proliferation was monitored by measuring the fluorescence intensity after 50 min staining using a Multi-Well Plate Reader (Gemini, Molecular Devices, Sunnyvale, Calif.). After proliferation reading, plates were washed once with basal medium to remove residual stain and cell morphology changes were observed using an inverted fluorescent microscope (Nikon Eclipse TE200, Nikon Instruments Inc., Melville, N.Y.) equipped with a digital imaging acquisition system (Spot digital camera with Spot Software V.2.1. for image capture, Nikon).

Analysis of cell differentiation (chondrogenesis and osteogenesis): In order to analyze the potential HMSC chondrogenic or osteogenic differentiation in presence of PDGF released from fibrin gels, cells were stained with Alcian Blue (for chondrogenesis) or Alizarin Red (for osteogenesis) after 1, 4 and 7 days of culture. Staining intensity of the cells incubated with medium from gels with added PDGF was compared to that of cells incubated with medium from gels without added PDGF and to cells incubated with freshly prepared medium with the addition of 30 ng of PDGF (positive control).

For Alcian Blue staining, cells were rinsed twice with Phosphate Buffer Solution (PBS) (Invitrogen Corporation, San Diego, Calif.), fixed with paraformaldehyde (Sigma Aldrich Inc.) for 10 min, and stained with 1% Alcian Blue (Sigma Aldrich Inc.) in 0.1N HCl for 30 min. Cells were rinsed 5 times (2 min each) with PBS and observed under an inverted light microscope (Nikon Eclipse TE200) equipped with a digital imaging acquisition system (previously described Spot digital camera with Spot Software V.2.1. for image capture, Nikon). For Alizarin Red staining, cells were first rinsed twice with PBS, fixed in ice-cold 70% ethanol for 10 min and stained with 2% Alizarin Red (Sigma Aldrich Inc.) in PBS for 30 min. Cells were then rinsed 5 times (2 min each) with PBS and observed using the inverted light microscope described above.

In addition to the staining by Alizarin Red, alkaline phosphatase (ALP) activity was measured as a marker of early osteogenic differentiation after 1, 4 and 7 days of culture. Cells in 12 well-culture-plates were washed twice with HBSS (Lonza Walkersville, Inc.) and trypsinized for a few minutes to detach them. Cells in suspension were then transferred in Eppendorf tubes and wells were washed with 0.5 ml of basal medium, then transferred in the corresponding Eppendorf tubes. Cells were then centrifuged for 5 min and washed once with 0.5 ml Tyrode's salt solution containing $NaHCO_3$ (Sigma Aldrich, Inc.). Supernatants were discarded, cell pellets were resuspended in 50 µl AMP-buffer+$MgCl_2$ (Sigma Aldrich, Inc.) and transferred into a 96-well plate. Tubes were washed with 25 µl AMP-buffer+$MgCl_2$, which were transferred into the corresponding wells of the 96-well plate. 75 µl of AMP-buffer+$MgCl_2$ were added to 3 wells of the 96-well plate and served as the blank. Finally, 75 µl of p-NPP (p-Nitrophenyl Phosphate, Sigma Aldrich, Inc.) stock substrate solution were added in each well and the plate was then placed at 37° C. for 30 min. The absorbance at 405 nm of p-nitrophenol product formed, which is proportional to ALP activity, was analyzed at 30 minutes using a Micro Plate Reader (Thermomax, Molecular Devices Corp.). Results, first measured as IU/L, were normalized on proliferation.

Effects of PDGF-BB on HMSC Seeded into Fibrin Gels:

In order to analyze the biological effects of PDGF-BB added in fibrin gels on the behavior of HMSC seeded into the fibrin gels and Human Umbilical Vascular Endothelial Cells (HUVEC, Lonza Walkersville, Inc.) seeded on the gel surface, TISSEEL VH S/D gels containing 10 mg/ml of FC and 2 IU/ml of Thrombin (final concentrations in the gels) were prepared with single culture cells (HMSC or HUVEC) or co-culture cells at a HMSC:HUVEC ratio of 4:1. PDGF-BB (60 ng/0.3 ml gel) was added in the FC in half of the co-culture gels at the time of gel preparation in order to compare cell behavior in gels with and without added PDGF-BB. Gels, prepared in 24-well-culture plates, were incubated at 37° C. in 5% $CO_2$ for up to 21 days using an endothelial cell growth medium (1 ml/gel) containing a serum supplement. Analysis of cell morphology and proliferation, as well as osteogenic differentiation, was performed at days 1, 7, 14 and 21. Cell morphology including the reorganization of HUVEC into interconnected cell-cell networks (early events of angiogenic differentiation) was observed by fluorescence microscopy after staining with Calcein dye. Cell proliferation was analyzed after staining with Calcein dye by measuring the overall fluorescence intensity of the cell suspensions after gel dissolution in a purified, concentrated bovine Trypsin solution. Finally, ALP was measured as an early marker of osteogenic differentiation (protocol described above) after resuspension of the cells following gel dissolution in a purified, concentrated bovine Trypsin solution.

Binding of PDGF by Surface Plasmon Resonance:

Surface Plasmon Resonance (SPR) is a technique that measures bimolecular interactions in real time. The analysis can determine if a specific analyte binds to a given ligand and determine the binding affinity and stoichiometry of the analyte binding to the ligand. The basic experimental approach is to first couple a gold plated chip with a ligand. The analyte, prepared in buffer (mobile phase), is then injected into a flow cell, where it is carried over the coated chip by a stream of buffer. If a bimolecular interaction occurs between the analyte and the ligand, the local increase in mass at the surface results in an increase in refractive index units (µRIU) on the metal surface. The change in (µRIU) can be graphed as a function of time.

In the present study, recombinant human PDGF-AB and recombinant human PDGF-BB were used as analytes, and the FC component of TISSEEL VH S/D was used as the ligand. Phosphate buffer solution (PBS, i.e. physiological salt condition solution) was used as the buffer. Different concentrations of each of the PDGF isoforms were passed separately over the surface of a FC-coated sensor chip. For each experiment and for each concentration, the association and dissociation rates were measured.

Statistical Analysis:

Release kinetics were conducted in triplicate. Results on proliferation, ALP activity, Alcian Blue and Alizarin staining are representative of 3 sets of experiments. Proliferation and ALP activity were conducted in triplicate and staining experiments in duplicate. SPR analysis for each PDGF concentration was conducted in triplicate. Statistical analysis was performed using the ANOVA test with 5% as the level of significance.

Example 2

Effects of PDGF Concentration on its Release Kinetics from TISSEEL VH S/D

The effects of PDGF concentration on its release kinetics from fibrin gels were analyzed using a single fibrin gel formulation (FC concentration of 20 mg/ml and Thrombin concentration of 2 IU/ml, final concentration in the gels) made of TISSEEL VH S/D. Release kinetic studies showed that PDGF-AB and BB release amount increased with the amount of growth factor initially added to the FC component of TISSEEL VH S/D (FIGS. 1 and 2).

Overall, cumulative release results showed that only about 20% to 35% of the initially added PDGF-AB was released after 10 days (FIG. 1). If considering the cumulative release of PDGF-AB after only 3 days, the cumulative release of PDGF-AB was approximately 8-13%. In other words, these results showed a retention of about 65-80% at day 10 and about 87-92% at day 3.

Figure 2:
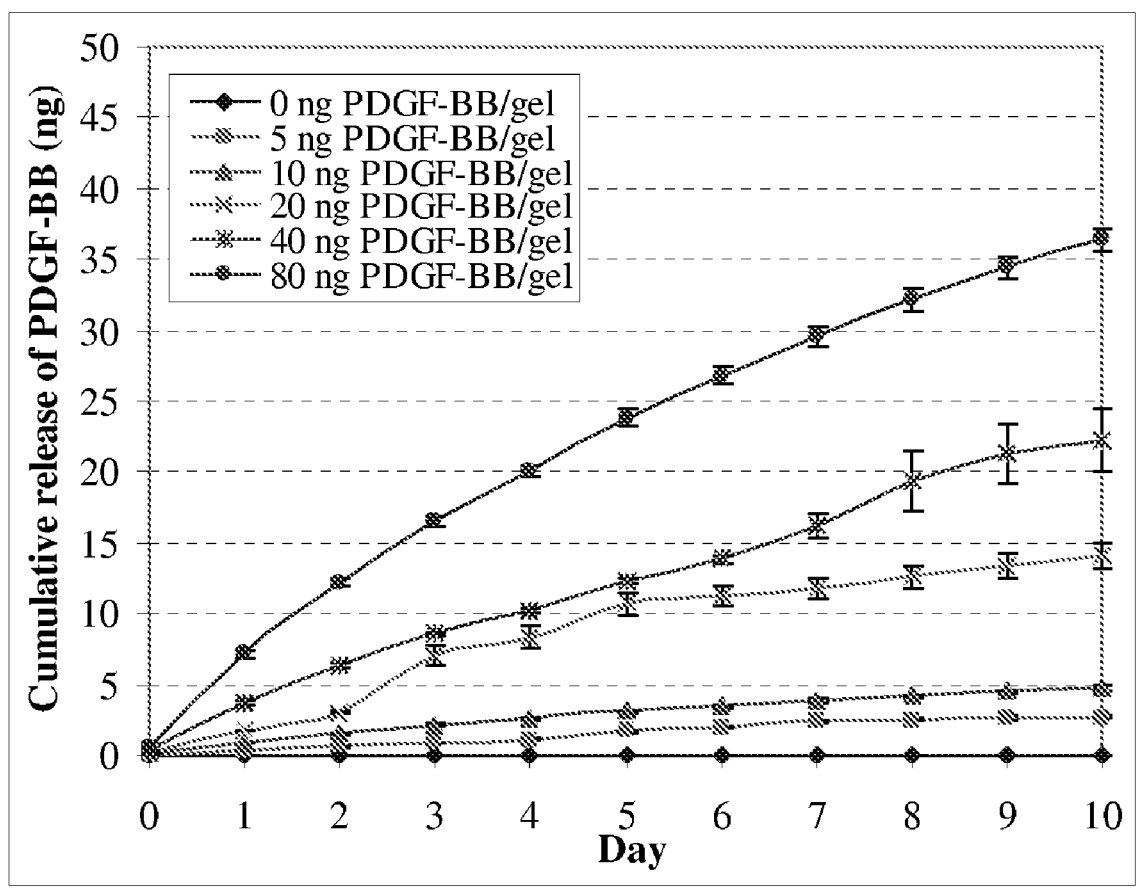
FIG. 2 shows the effects of PDGF-BB amount on its cumulative release from TISSEEL VH S/D gels ([FC]=20 mg/ml and [Thrombin]=2 IU/ml).

Results with PDGF-BB followed the same trends, but depicted a higher overall release, with about 45% to 70% released after 10 days (FIG. 2). If considering the cumulative release of PDGF-BB after only 3 days, the cumulative release was approximately 20-35%.

These results suggest a strong binding interaction of both PDGF-AB and BB with fibrin.

Example 3

Effects of FC Concentration on PDGF Release Kinetics from TISSEEL VH S/D

To determine the effects of FC concentration on the PDGF release kinetics when using TISSEEL VH S/D Fibrin Sealant, release was analyzed using gels having a fixed Thrombin concentration (2 IU/ml) over four different FC concentrations (5, 10, 20 and 40 mg/ml, final concentrations in the gels) of TISSEEL VH S/D.

Figure 3A:
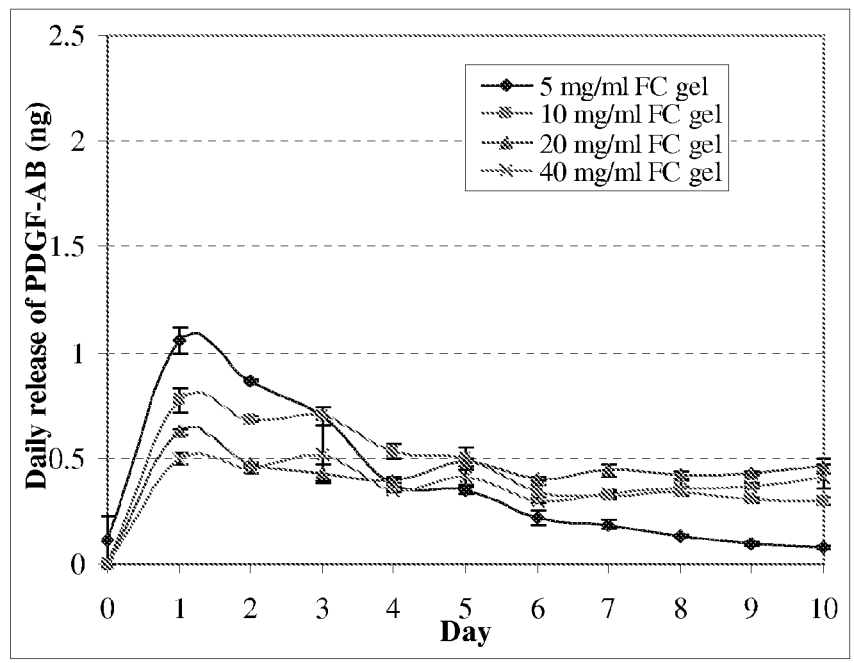
FIG. 3 shows the effects of FC concentration on PDGF-AB daily release (FIG. 3A) and cumulative release (FIG. 3B) from TISSEEL VH S/D gels ([Thrombin]=2 IU/ml).
Figure 3B:
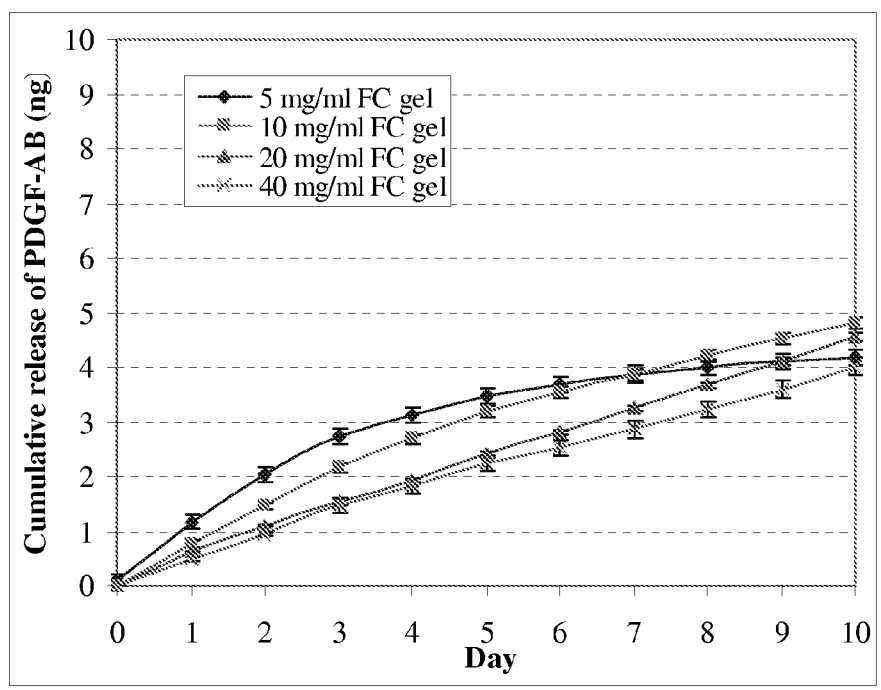

ELISA results showed a spike release at day 1 and a decrease in the release up to day 10 for all concentrations of FC analyzed (FIG. 3A). When adding 15 ng of PDGF-AB in the gels, the FC concentration (from 5 to 40 mg/ml) did not significantly influence the release kinetics. The cumulative release showed that approximately 27% to 32% of the initial amount (15 ng) was released after 10 days (FIG. 3B) and only 10% to 20% after 3 days. In other words, the retention was about 70% after 10 days, up to 80-90% after only 3 days, and was not influenced by FC concentration, suggesting that 5 mg/ml of FC was enough to bind 15 ng of PDGF-AB.

Figure 4A:
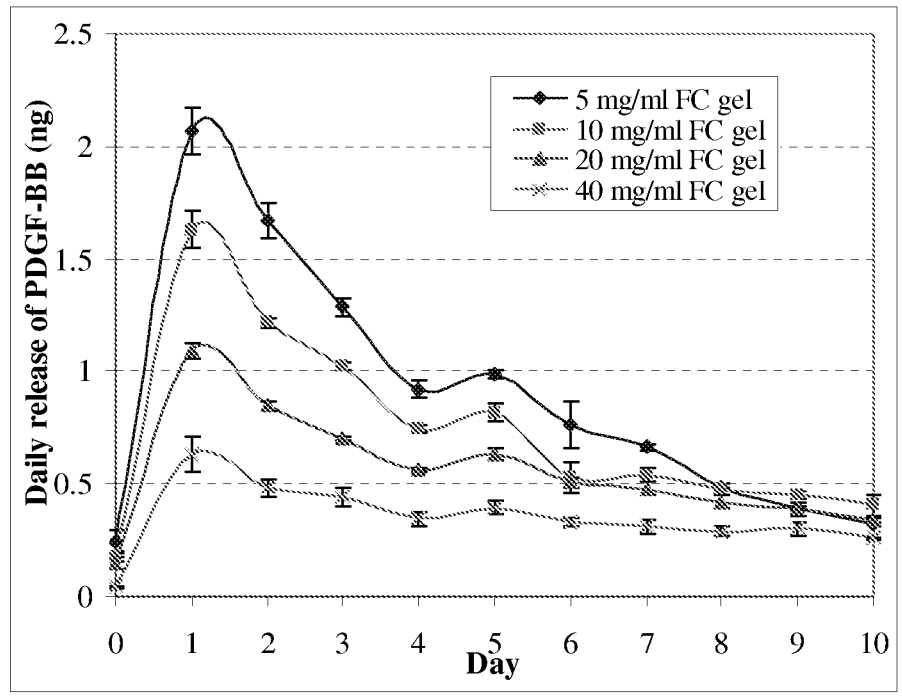
FIG. 4 shows the effects of FC concentration on PDGF-BB daily release (FIG. 4A) and cumulative release (FIG. 4B) from TISSEEL VH S/D gels ([Thrombin]=2 IU/ml).
Figure 4B:
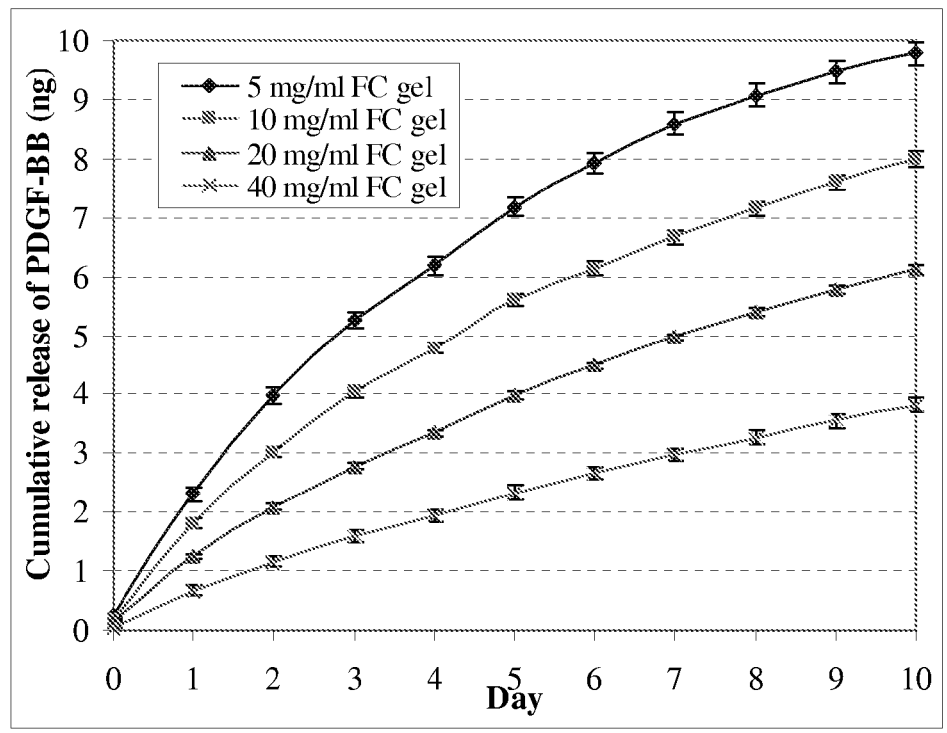

Results with PDGF-BB, however, showed an effect of FC concentration on the overall release percentage (FIG. 4). Indeed, PDGF-BB cumulative release from TISSEEL VH S/D was higher with lower FC concentrations (about 65% with 5 mg/ml and 25% with 40 mg/ml of FC) at day 10. Analysis of cumulative release at day 3 also showed a dependence on FC concentration, with approximately 35% released with 5 mg/ml of FC and 10% released with 40 mg/ml of FC. In other words, these results showed a minimum retention of about 35% (with 5 mg/ml of FC) and a maximum retention of about 75% (with 40 mg/ml of FC) after 10 days, and a minimum retention of about 65% and maximum of about 90% after 3 days. The dependence of the release kinetics on FC concentration suggests a possible controlled release of PDGF-BB by changing FC concentration.

After dissolving the gels to recover PDGF-AB remaining in the gels, ELISA results showed that at least 85% of the initially added amount of PDGF-AB was recovered. After dissolving the gels to recover PDGF-BB remaining in the gels, ELISA results showed that 65% to 75% of the initially added amount of PDGF-BB was recovered. Since the recovery was not complete for PDGF-BB, the release percentages of PDGF-BB might be slightly underestimated.

Example 4

Effects of Using Different Product Lots of TISSEEL VH S/D

Figure 5:
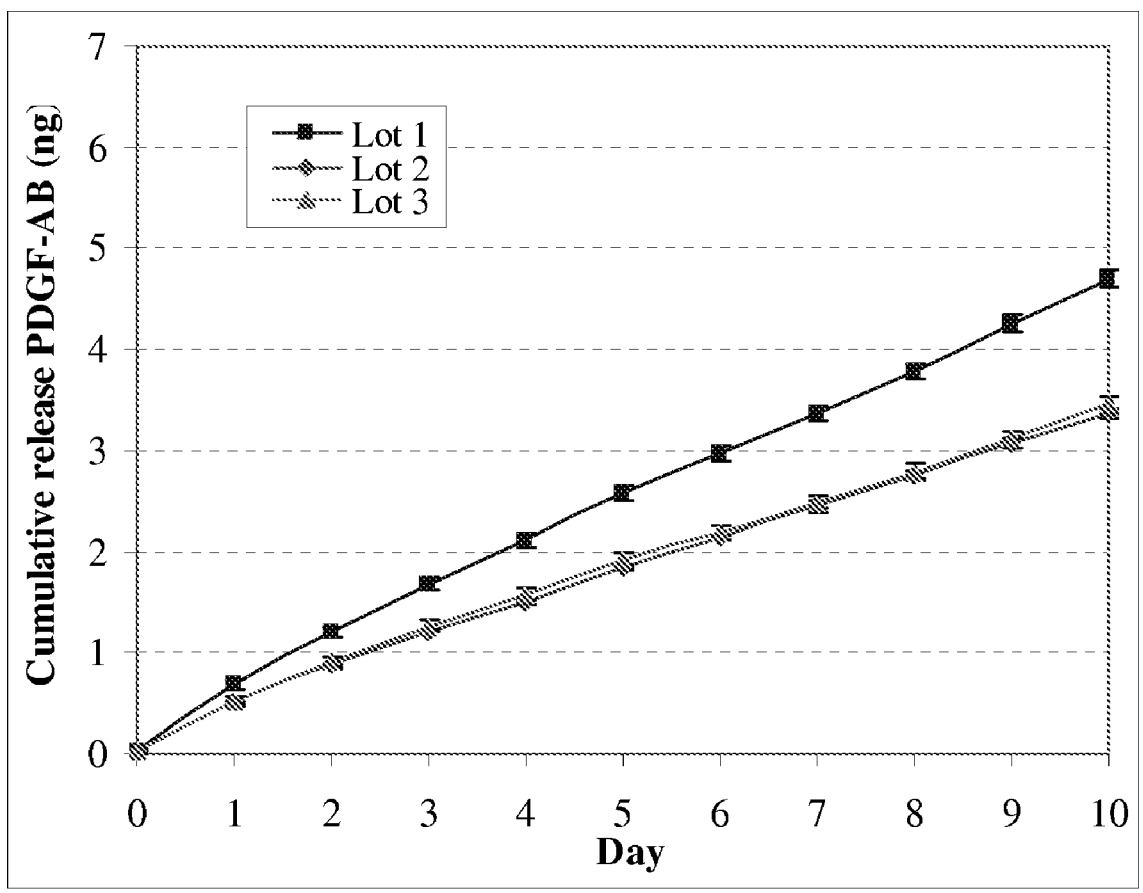
FIG. 5 shows the effects of TISSEEL VH S/D lot number on PDGF-AB cumulative release ([FC]=20 mg/ml, [Thrombin]=2 IU/ml).
Figure 6:
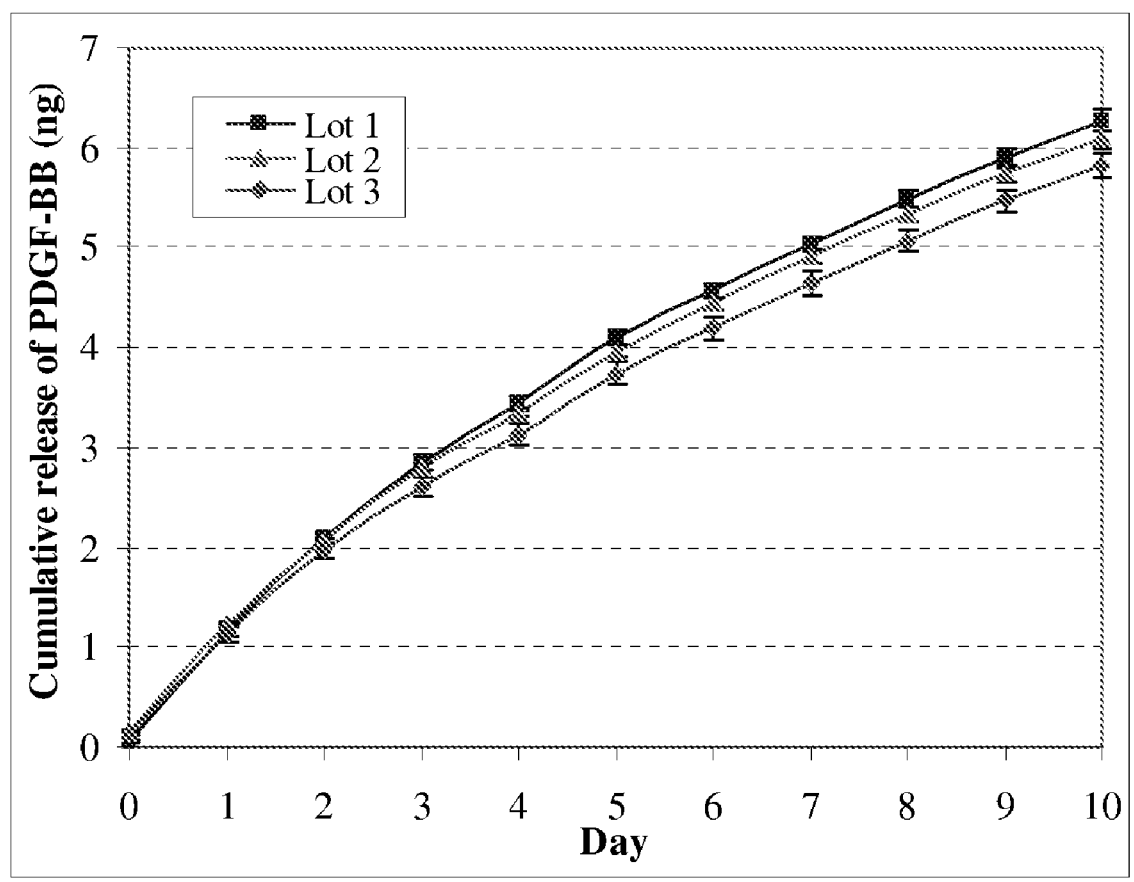
FIG. 6 shows the effects of TISSEEL VH S/D lot number on PDGF-BB cumulative release ([FC]=20 mg/ml, [Thrombin]=2 IU/ml).

When looking at the effects of using different FC product lots from TISSEEL VH S/D with a single gel formulation (20 mg/ml of FC and 2 IU/ml of Thrombin, final concentrations in the gels), results showed a constant release up to day 10 for all lots analyzed. The cumulative release of PDGF-AB after 10 days ranged from about 23% to 32%, depending on the FC lot (FIG. 5), and was, therefore, similar for the 3 lots. The cumulative release of PDGF-BB after 10 days ranged from about 38% to 42%, depending on the FC lot (FIG. 6), and was, therefore, also similar for the 3 lots.

These results show that there is not a significant difference in PDGF release between fibrin lots and therefore there should be little worry about lot to lot variation in release kinetics.

After dissolving the gels to recover PDGF-AB remaining in the gels, ELISA results showed full recovery of the initial added amount of PDGF-AB. After dissolving the gels to recover PDGF-BB remaining in the gels, ELISA results showed that about 65% of the initially added amount of PDGF-BB was recovered. Since the recovery was not complete for PDGF-BB, the overall release percentages for PDGF-BB may be slightly underestimated.

Example 5

Release Kinetics of PDGF-BB from TISSEEL VH

Release kinetics of PDGF-BB from TISSEEL VH was analyzed to observe potential differences when using TISSEEL VH and TISSEEL VH S/D.

Figure 7:
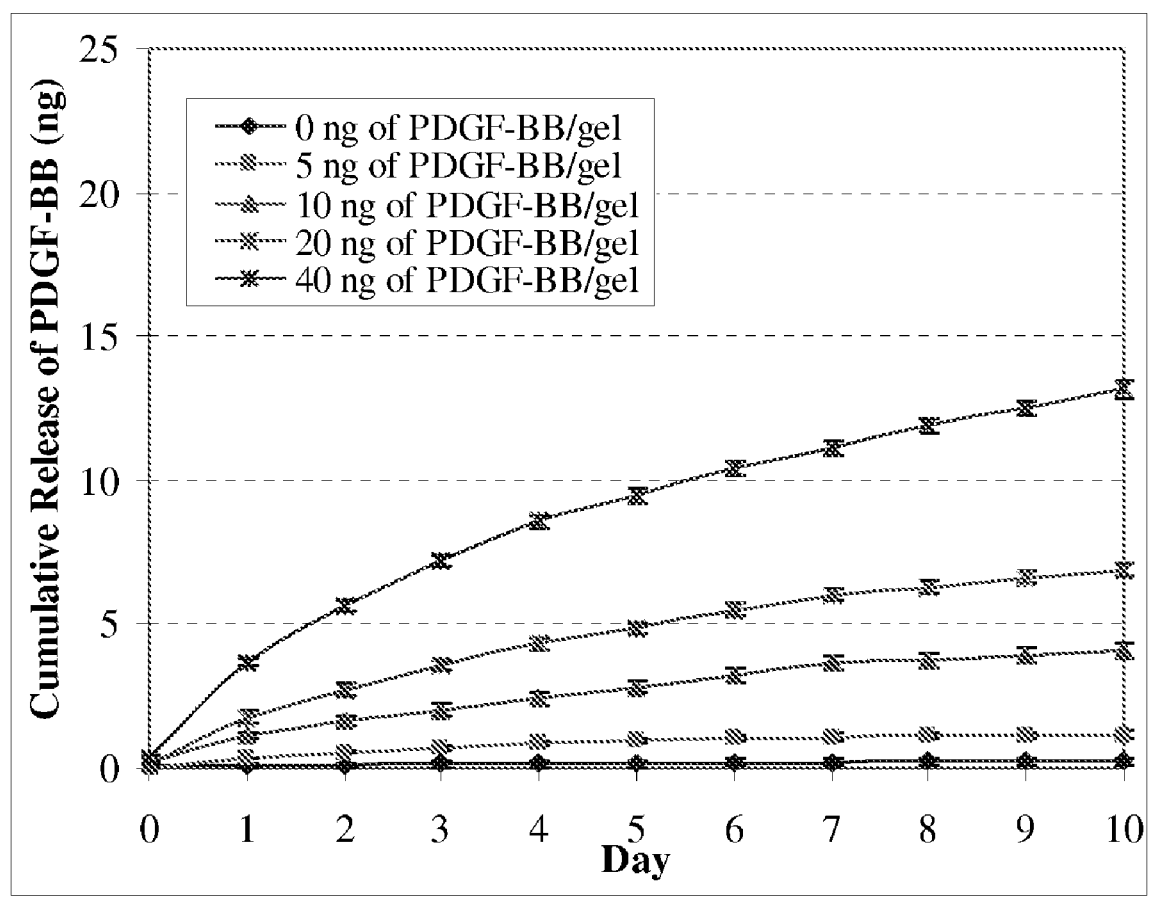
FIG. 7 shows the effects of PDGF-BB amount on its cumulative release from TISSEEL VH gels ([FC]=20 mg/ml and [Thrombin]=2 IU/ml).

The effects of PDGF-BB concentration on the release kinetics from TISSEEL VH were measured. Results showed that the released amount increased with the amount of growth factor initially added to the FC component (FIG. 7). Overall, the cumulative release results showed that only about 20% to 40% of the initially added PDGF-BB was released after 10 days, i.e., about two times lower than the release observed when using TISSEEL VH S/D. After only 3 days, results showed a cumulative release of PDGF-BB of about 15-20%. However, it should be noted that these values might be underestimated as experiments with TISSEEL VH were conducted with polystyrene plates (compared to polypropylene tubes for TISSEEL VH S/D), and PDGF may bind non-specifically to the polystyrene plates. Recovery of the growth factor remaining in the gels at the end of the 10-day release experiment was not measured to confirm this potential underestimation.

Figure 8A:
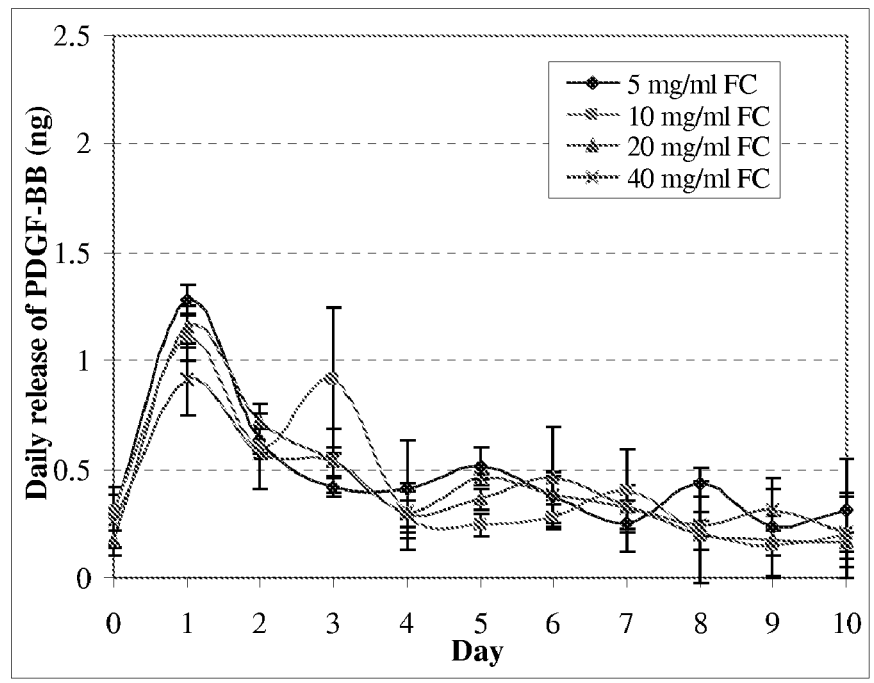
FIG. 8 shows the effects of FC concentration on PDGF-BB daily release (FIG. 8A) and cumulative release (FIG. 8B) from TISSEEL VH gels ([Thrombin]=2 IU/ml).
Figure 8B:
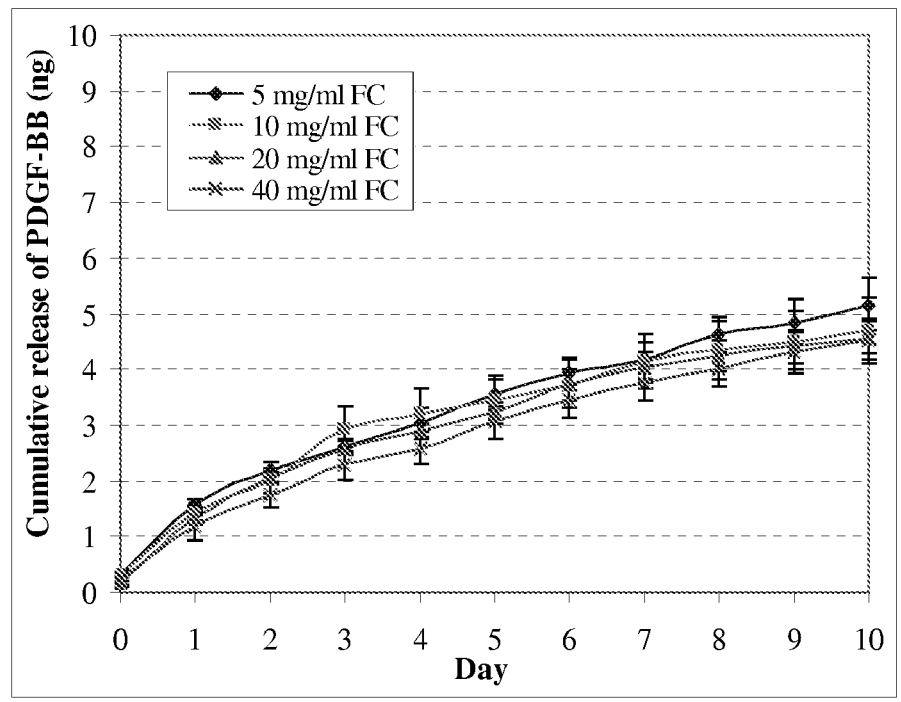

When looking at the effect of FC concentration on daily PDGF-BB release from TISSEEL VH, ELISA results showed a spike release at day 1 and a decrease in the release up to day 10 for all concentrations analyzed (FIG. 8A). Results also showed that, when adding 15 ng of PDGF-BB in TISSEEL VH gels, the FC concentration (from 5 to 40 mg/ml) did not influence the release kinetics and the cumulative release showed that about 30% to 35% of the initial added amount (15 ng) was released after 10 days (FIG. 8B). This result suggests that 5 mg/ml of FC from TISSEEL VH was enough to bind 15 ng of PDGF-BB. However, as for the results on the effects of PDGF-BB concentration, it should be noted that these values with TISSEEL VH might be underestimated due to the use of polystyrene plates.

Figure 9:
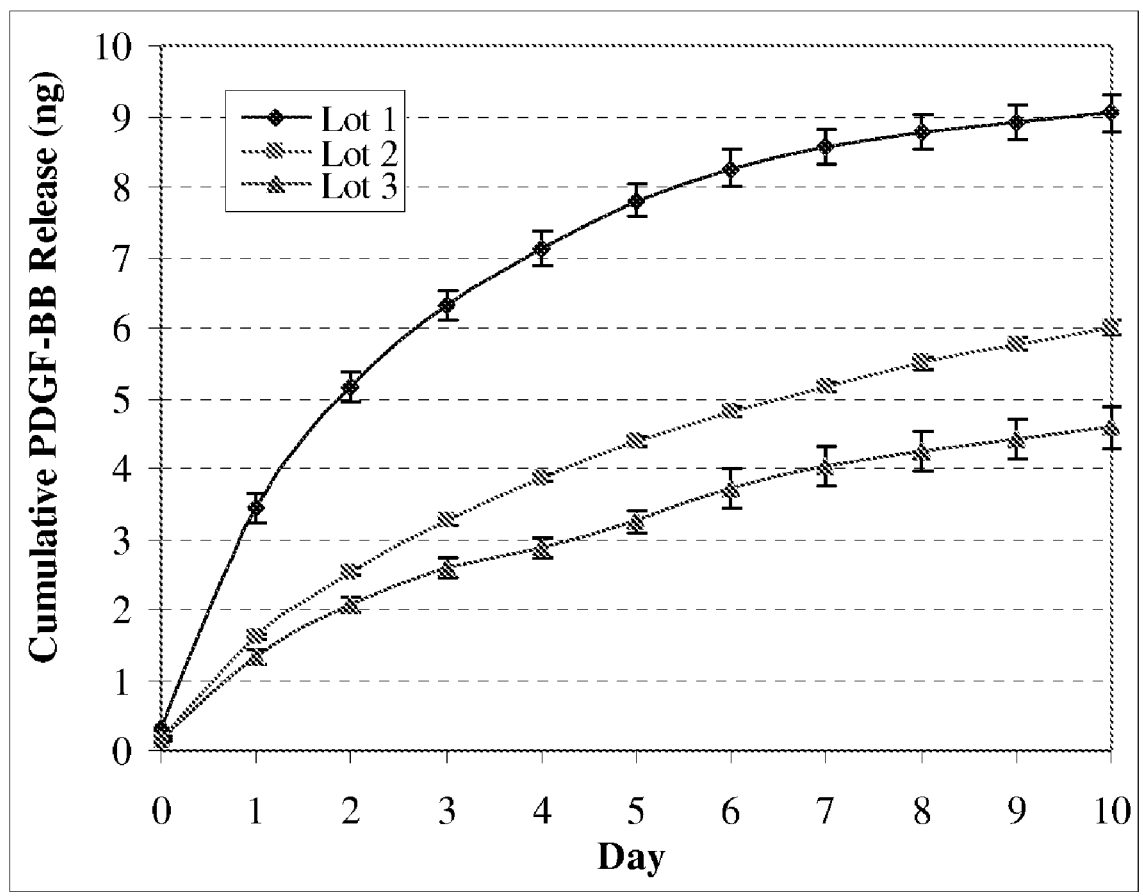
FIG. 9 shows the effects of TISSEEL VH lot number on PDGF-BB cumulative release ([FC]=20 mg/ml, [Thrombin]=2 IU/ml).

Finally, when looking at the effects of using different FC product lots from TISSEEL VH with a single gel formulation (20 mg/ml of FC and 2 IU/ml of Thrombin, final concentrations in the gels), results showed a constant release up to day 10 for all lots analyzed. The cumulative release of PDGF-BB after 10 days ranged from about 30% to 60% (FIG. 9), and was therefore dependent on the FC lot number, which was opposite to the results found with TISSEEL VH S/D. One of the difference between the 3 lots of TISSEEL VH analyzed is the content of Factor XIII (negligible for lot 1, 33.9 U/ml for lot 2 and 42.2 IU/ml for lot 3), suggesting a potential correlation between the amount of Factor XIII and the release rate of PDGF-BB from TISSEEL VH.

Example 6

Biological Activity of Released PDGF on HMSC Monolayers In Vitro

Human mesenchymal stem cells (HMSC) are pluripotent progenitor cells that can differentiate into different specialized tissue cell types including chondrocytes, osteoblasts, adipocytes and myocytes (Caplan A I, J Orthop Res 9: 641-

650, 1991). The commitment and differentiation of these cells are modulated by a variety of factors, including cell interactions but also specific growth factors. PDGF family members have been identified as regulators of MSC maturation.

The effects of released growth factor on HMSC was measured. As stated in the Materials and Methods section, medium supernatants were collected from the fibrin gels (120 ng of PDGF-AB and 60 ng of PDGF-BB were added in the FC component before polymerization for gels with added PDGF) at day 3 (without changing the medium every day) and were used as culture medium for HMSC monolayers. Some of the gels were prepared without added PDGF for control samples in order to insure that any changes observed with medium from gels with added PDGF were indeed induced by the released PDGF and not by some other potential bioactive components that could have been released from the gels themselves.

HMSC cultured with medium supernatants from TISSEEL VH S/D gels with added PDGF-AB or PDGF-BB, i.e. medium containing released PDGF (gels initially prepared with 20 mg/ml of FC, 2 IU/ml of Thrombin) showed changes in cell morphology as early as day 4 and even more pronounced at day 7. They had a more elongated shape than those cultured with medium supernatants from gels without added PDGF and were more similar to those cultured with medium containing freshly added PDGF. Effects were even more pronounced with PDGF-BB.

Figure 10:
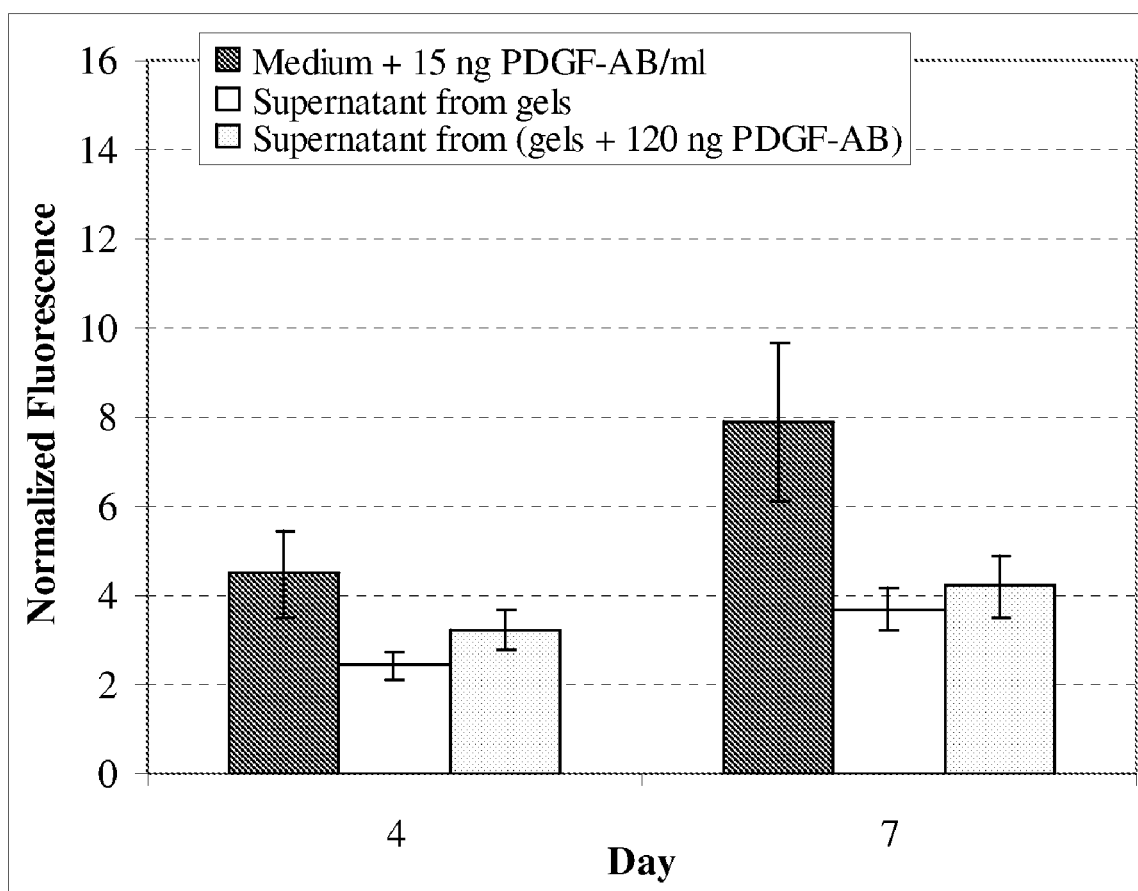
FIG. 10 shows the effects of PDGF-AB released from TISSEEL VH S/D gels on HMSC proliferation cultured in monolayer up to 7 days.
Figure 11:
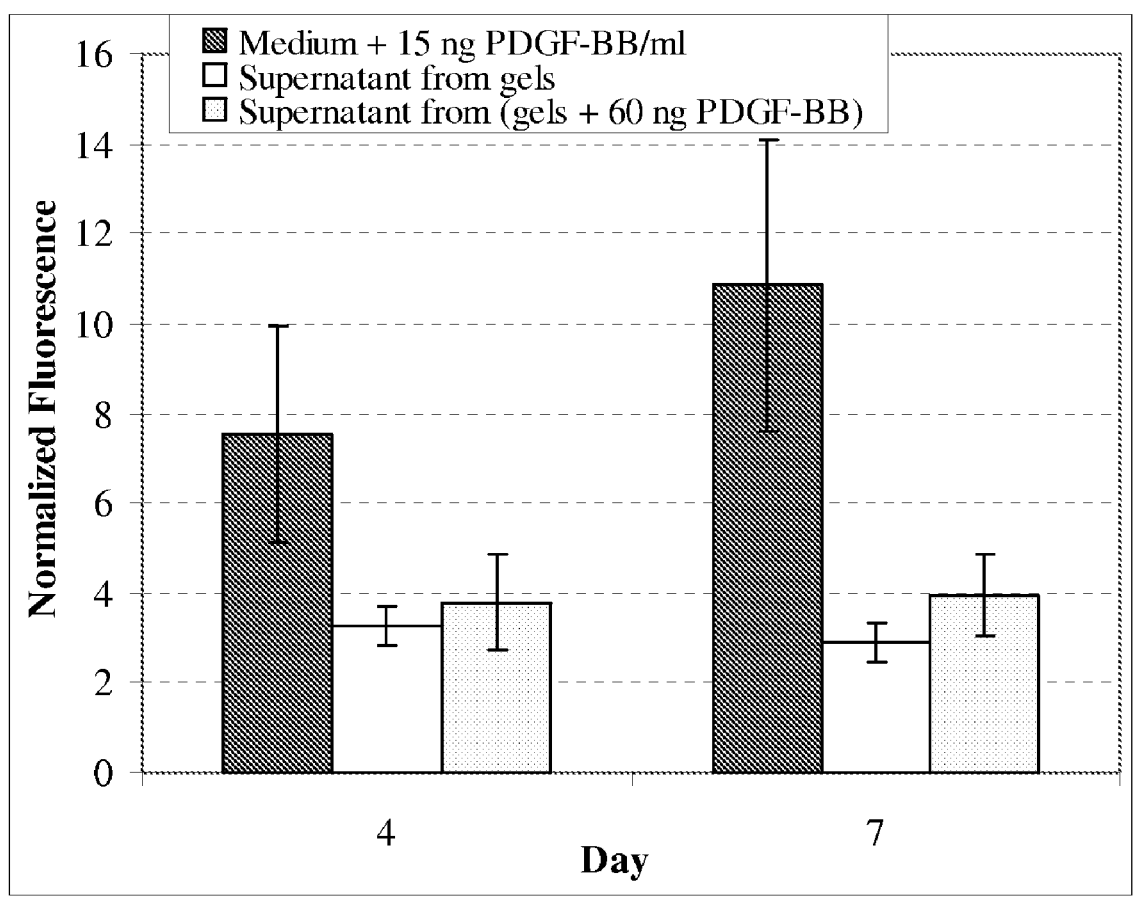
FIG. 11 shows the effects of PDGF-BB released from TISSEEL VH S/D gels on HMSC proliferation cultured in monolayer up to 7 days.

Cell proliferation at days 4 and 7 were normalized to proliferation at day 1 (baseline). HMSC proliferation tended to increase when cultured for 7 days with medium supernatants from TISSEEL VH S/D gels with added PDGF (i.e. medium containing released PDGF), but the difference was not significant (p>0.05) (FIGS. 10 and 11). Proliferation of cells cultured with medium with freshly added PDGF was significantly higher.

Figure 12:
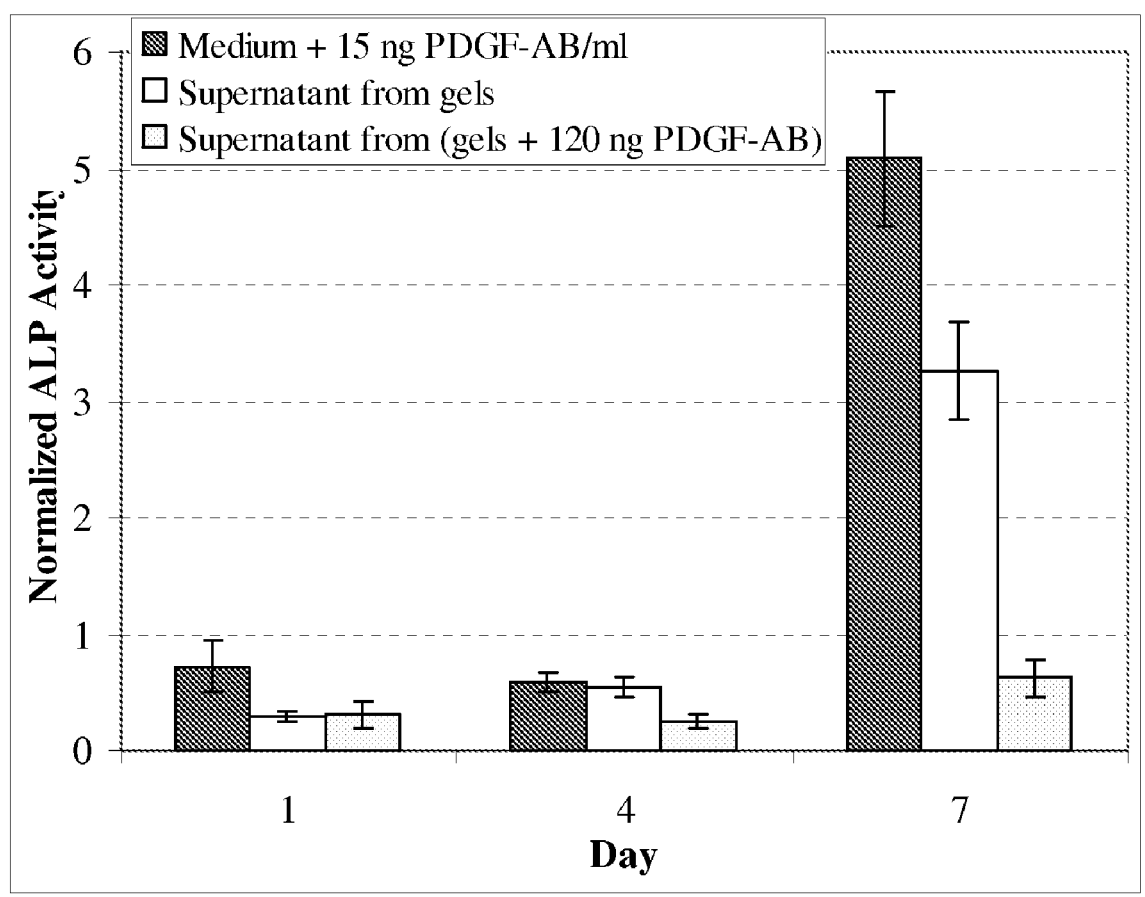
FIG. 12 shows the effects of PDGF-AB released from TISSEEL VH S/D gels on ALP activity (normalized on proliferation).
Figure 13:
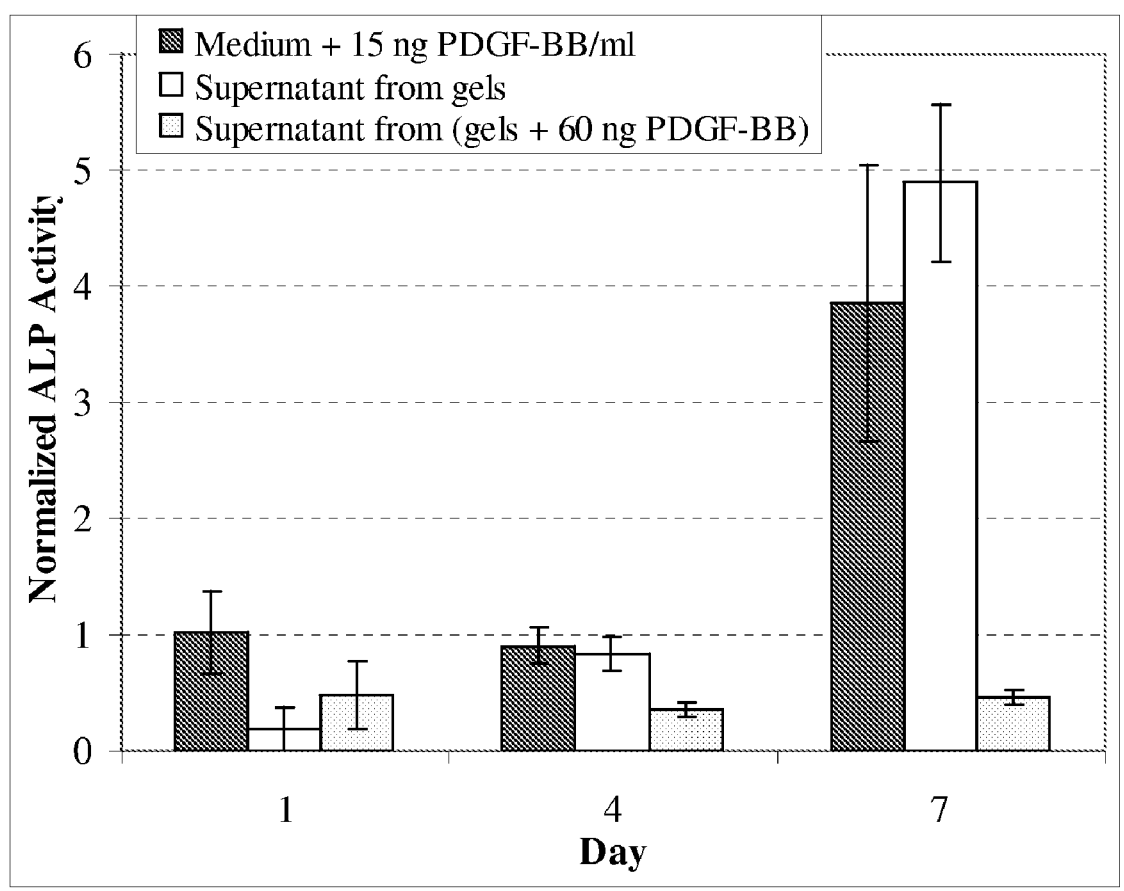
FIG. 13 shows the effects of PDGF-BB released from TISSEEL VH S/D gels on ALP activity (normalized on proliferation).

Alkaline phosphatase (ALP) activity in HMSC cultured with supernatants from TISSEEL VH S/D gels with added PDGF was significantly lower than that in HMSC cultured with supernatants from TISSEEL VH S/D gels without added PDGF and with medium containing freshly added PDGF (FIGS. 12 and 13).

Both Alcian blue (indicator of chondrogenic differentiation) and Alizarin Red (indicator of late osteogenic differentiation) were negative at all time points up to 7 days.

In general, all the observed changes in HMSC behavior in the presence of released PDGF from TISSEEL VH S/D fibrin gels were more pronounced with PDGF-BB. Overall, results showed that released PDGF from TISSEEL VH S/D fibrin gels was still biologically active, inducing mainly a change in HMSC morphology and an inhibition of ALP activity.

Example 7

Effects of PDGF-BB on HMSC Seeded Inside Fibrin Gels and HUVEC Seeded on the Surface of Fibrin Gels In order to analyze the effects of PDGF on the behavior of HMSC seeded into fibrin gels and Human Umbilical Vascular Endothelial Cells (HUVEC, Lonza Walkersville Inc.) seeded on the gel surface, gels comprising the cells were prepared as described in the Materials and Methods.

Briefly, gels containing 10 mg/ml of FC and 2 IU/ml of Thrombin (final concentrations in the gels) were prepared with single culture cells (HMSC or HUVEC) or co-culture cells at a HMSC:HUVEC ratio of 4:1. Recombinant PDGF-BB (60 ng/0.3 ml gel) was added in the FC in half of the co-culture gels at the time of gel preparation. Gels were incubated at 37° C. in 5% $CO_2$ for up to 21 days using an endothelial cell growth culture medium (Lonza Walkersville Inc.) containing a serum supplement. Analysis of cell morphology and proliferation, as well as osteogenic differentiation, was performed at days 1, 7, 14 and 21.

Fluorescence microscopy analysis showed that, with time, HMSC were evenly dispersed, in higher number, and had a more elongated shape when seeded in single culture gels. They were also evenly dispersed and elongated in co-culture gels with added PDGF-BB whereas they were smaller, in lower number, and tended to migrate towards the bottom of the co-culture gels without added PDGF-BB. HUVEC reorganization into interconnected cell-cell networks (early events of angiogenesis) started earlier and happened to a larger extent in single culture gels and co-cultured gels containing additional PDGF-BB compared to co-culture gels without added PDGF-BB.

Cell proliferation increased with time. No significant difference was observed between gels with and without added PDGF-BB, but a tendency for higher proliferation was noticed at days 7 and 14 in gels containing added PDGF-BB. ALP activity remained at low levels, indicating that PDGF-BB added in the gels did not induce osteogenic differentiation of the HMSC seeded in the gels.

Example 8

Binding of PDGF by Surface Plasmon Resonance (SPR)

Figure 14:
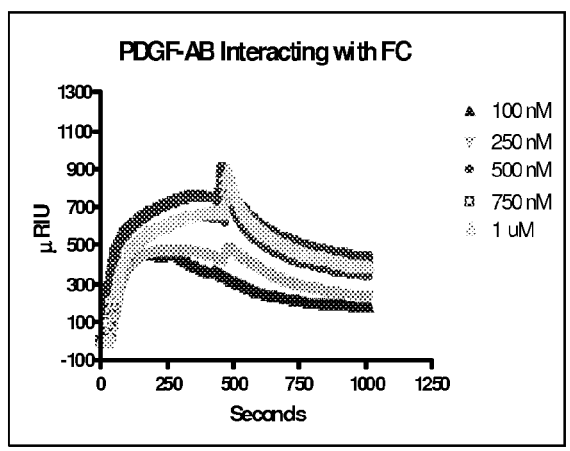
FIG. 14 depicts a sensorgram of PDGF-AB (FIG. 14A) and PDGF-BB (FIG. 14B) interacting with FC from TISSEEL VH S/D.
Figure 14:
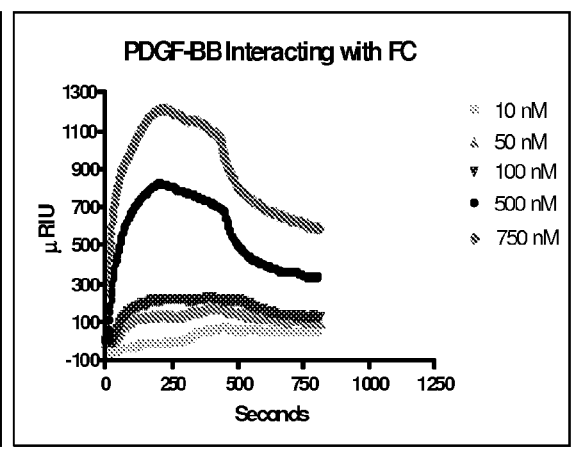
Figure 14:
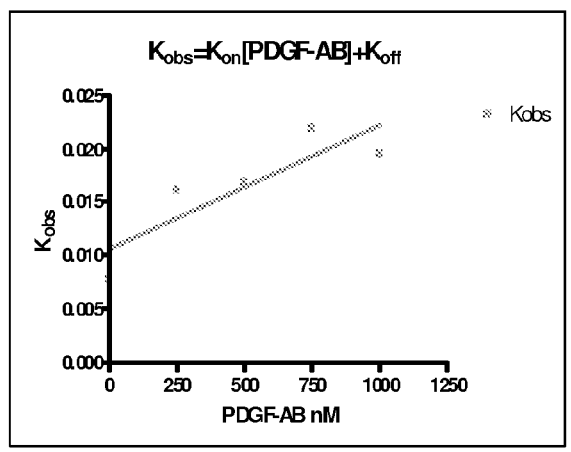

SPR was used to characterize the interactions between PDGF-AB and PDGF-BB with the FC component of TISSEEL VH S/D. The sensorgrams of the interactions are shown in FIGS. 14A-14B. The association and dissociation parts of the curve were plotted and fitted to a one-phase exponential association and dissociation curve, respectively, using non-linear regression analysis (FIG. 14C). As FIG. 14B indicates, the disassociation curve for PDGF-BB is biphasic. This did not allow the accurate determination of the $K_D$ value for the interaction between PDGF-BB and the FC component of TISSEEL VH S/D. However, SPR was successfully used to calculate the $K_D$ value for PDGF-AB interactions with FC component of TISSEEL VH S/D (in the presence of buffer (PBS, pH 7.4)). The analysis of the association phase of the sensorgrams provided the rate constants ($K_{obs}$), which were plotted versus the analyte concentration (FIG. 14C). These plots were analyzed by linear regression to obtain the slopes and intercepts, which correspond to the association rate ($K_{on}$) and the dissociation rate ($K_{off}$) constants, respectively. The equilibrium dissociation constant ($K_D$) was calculated by dividing the dissociation rate constants by the association rate constants.

The equilibrium dissociation constant ($K_D$) was also determined by a complementary method, which relied upon the dissociation phase of the binding sensorgrams. In this method, the dissociation rate constants ($K_{off}$) for PDGF-AB were calculated from the non-linear regression analysis of the dissociation phase of the sensorgram. The dissociation equilibrium constant ($K_D$) was measured by dividing the dissociation rate constant ($K_{off}$) by the association rate constant ($K_{on}$) (which were obtained from the analysis of the association phase of the sensorgrams).

Using both methods, the $K_D$ value for PDGF-AB binding to the FC component of TISSEEL VH S/D was 342±41 nM.

Summary

The release kinetic measured above showed that added recombinant PDGF in fibrin gels is gradually released from the gels, suggesting a binding interaction of PDGF with fibrin (ogen). This binding interaction was further confirmed by a cumulative release after 10 days that was lower than the initial added amount of PDGF. PDGF-BB appeared to be released faster than PDGF-AB (lower retention of PDGF-BB) and FC concentration appeared to influence PDGF-BB release rate from TISSEEL VH S/D fibrin gels, suggesting that varying FC concentration could be used to control the release rate of PDGF-BB. Overall, these results suggest a binding interaction of these two forms of PDGF with fibrin, especially PDGF-AB. Using SPR, results showed that both PDGF-AB and PDGF-BB bind to the FC component of TISSEEL. Finally, biological activity results demonstrated that released PDGF was still biologically active, inducing mainly a change in HMSC morphology but no osteogenic and/or chondrogenic differentiation.

In conclusion, the present study suggests that fibrin gels are a potential carrier system to deliver bioactive PDGF and demonstrated an intrinsic property of the FC component of TISSEEL Fibrin Sealant to bind PDGF-AB and BB.

Numerous modifications and variations of the invention as set forth in the above illustrative examples are expected to occur to those skilled in the art. Consequently only such limitations as appear in the appended claims should be placed on the invention.

What is claimed:

1. A method for the controlled release of a platelet derived growth factor (PDGF) protein, said protein selected from the group consisting of PDGF-AB and PDGF-BB, in a patient in need thereof, comprising administering to a patient a fibrin sealant comprising PDGF, wherein at least 25% of the PDGF is retained in the fibrin sealant for at least 3 days, or wherein at least 20% of the PDGF is retained in the fibrin sealant for at least 10 days, wherein the fibrin sealant has a final fibrinogen complex concentration within the range of about 5 mg/ml to about 75 mg/ml.

2. The method of claim 1 wherein the fibrin sealant is produced by combining a fibrinogen complex (FC) component and a thrombin component in admixture.

3. The method of claim 2 wherein the PDGF is added to the FC component before admixture of the FC component with the thrombin component.

4. The method of claim 1 wherein at least 35% to 90% of the PDGF is retained for at least 3 days.

5. The method of claim 1 wherein at least 45% to 75% of the PDGF is retained in the fibrin sealant for at least 3 days.

6. The method of claim 1 wherein at least 60% of the PDGF is retained in the fibrin sealant for at least 3 days.

7. The method of claim 1 wherein the PDGF released is biologically active.

8. The method of claim 1 wherein at least 25% to 75% of the PDGF is retained for at least 10 days.

9. The method of claim 1 wherein at least 45% to 55% of said PDGF is retained in the fibrin sealant for at least 10 days.

10. The method of claim 2 wherein the final thrombin concentration in the sealant is within the range of about 1 IU/ml to 250 IU/ml.

11. The method of claim 2 wherein the final fibrinogen complex concentration is 40 mg/ml and the final thrombin concentration is about 2 IU/ml.

12. The method of claim 1 wherein the final PDGF concentration in the sealant is from about 1 ng/ml to about 1 mg/ml.

13. The method of claim 1 wherein the PDGF is PDGF-AB.

14. The method of claim 13 wherein at least 60% of said PDGF-AB is retained in said fibrin sealant for at least 3 days, and wherein at least 40% of said PDGF-AB is retained in said fibrin sealant for at least 10 days.

15. The method of claim 1 wherein the PDGF is PDGF-BB.

16. The method of claim 15 wherein at least 55% of said PDGF-BB is retained in said fibrin sealant for at least 3 days, and wherein at least 25% of said PDGF-BB is retained in said fibrin sealant for at least 10 days.

17. The method of claim 1 wherein the patient is suffering from a disease selected from the group consisting of a musculoskeletal disease or disorder, a soft tissue disease or disorder and a cardiovascular disease.

18. A method for treating a patient suffering from a disorder or disease which would benefit from in situ controlled release of a platelet derived growth factor (PDGF) protein, said protein selected from the group consisting of PDGF-AB and PDGF-BB, said method comprising administering to said patient a fibrin sealant comprising the PDGF protein, wherein the fibrin sealant provides a controlled release of the PDGF wherein at least 25% of the PDGF is retained in the fibrin sealant for at least 3 days, or wherein at least 20% of the PDGF is retained in the fibrin sealant for at least 10 days, and said PDGF is released at a rate effective to treat said disorder or disease, wherein the fibrin sealant has a final fibrinogen complex concentration within the range of about 5 mg/ml to about 75 mg/ml.

19. The method of claim 18 wherein the fibrin sealant is produced by combining a fibrinogen complex (FC) component and a thrombin component in admixture.

20. The method of claim 18 wherein the PDGF is added to the FC component before admixture of the FC component with the thrombin component.

21. The method of claim 18 wherein at least 35% to 90% of the PDGF is retained in the fibrin sealant for at least 3 days.

22. The method of claim 18 wherein at least 45% to 75% of the PDGF is retained in the fibrin sealant for at least 3 days.

23. The method of claim 18 wherein at least 60% of the PDGF is retained in the fibrin sealant for at least 3 days.

24. The method of claim 18 wherein at least 20% of said PDGF is retained in the fibrin sealant for at least 10 days.

25. The method of claim 18 wherein at least 25% to 75% of the PDGF is retained for at least 10 days.

26. The method of claim 18 wherein at least 45% to 55% of said PDGF is retained in the fibrin sealant for at least 10 days.

27. The method of claim 18 wherein the released PDGF is biologically active.

28. The method of claim 18 wherein the final thrombin concentration in the sealant is within the range of about 1 IU/ml to 250 IU/ml.

29. The method of claim 18 wherein the final fibrinogen complex concentration is about 40 mg/ml and the final thrombin concentration is about 2 IU/ml.

30. The method of claim 18 wherein the final PDGF concentration in the sealant is from about 1 ng/ml to about 1 mg/ml.

31. The method of claim 18 wherein the PDGF is PDGF-AB.

32. The method of claim 31 wherein at least 80% of said PDGF-AB is retained in said fibrin sealant for at least 3 days, and wherein at least 60% of said PDGF-AB is retained in said fibrin sealant for at least 10 days.

33. The method of claim 18 wherein the PDGF is PDGF-BB.

34. The method of claim 33 wherein at least 55% of said PDGF-BB is retained in said fibrin sealant for at least 3 days, and wherein at least 25% of said PDGF-BB is retained in said fibrin sealant for at least 10 days.

35. The method of claim 18 wherein the patient is suffering from a disease selected from the group consisting of a musculoskeletal disease or disorder, a soft tissue disorder and a cardiovascular disease.

* * * * *

UNITED STATES PATENT AND TRADEMARK OFFICE
CERTIFICATE OF CORRECTION

PATENT NO. : 8,377,864 B2
APPLICATION NO. : 12/142734
DATED : February 19, 2013
INVENTOR(S) : Catelas et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 976 days.

Signed and Sealed this
Ninth Day of December, 2014

Michelle K. Lee
*Deputy Director of the United States Patent and Trademark Office*